United States Patent
Maske et al.

(10) Patent No.: US 6,208,107 B1
(45) Date of Patent: Mar. 27, 2001

(54) USE OF DIGITAL CURRENT RAMPING TO REDUCE AUDIBLE NOISE IN STEPPER MOTOR

(75) Inventors: Rudolph J. Maske, San Jose; David M. Woods, El Dorado Hills, both of CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/454,001

(22) Filed: Dec. 3, 1999

(51) Int. Cl.$^7$ .................................................. G05B 19/40
(52) U.S. Cl. ............................ 318/685; 318/696; 417/45
(58) Field of Search ..................................... 318/685, 696, 318/138; 417/20, 22, 45; 388/815

(56) References Cited

U.S. PATENT DOCUMENTS

| | | | |
|---|---|---|---|
| 3,806,821 | 4/1974 | Niemeyer et al. | 328/34 |
| 3,886,459 | 5/1975 | Hufford et al. | 328/34 |
| 3,890,554 | 6/1975 | Yoshitake et al. | 318/696 |
| 3,909,693 | 9/1975 | Yoshitake et al. | 318/696 |
| 3,911,343 | 10/1975 | Oster | 318/392 |
| 3,919,608 | 11/1975 | Usami et al. | 318/738 |
| 4,333,045 | 6/1982 | Oltendorf | 318/696 |
| 4,477,756 | 10/1984 | Moriguchi | 318/696 |
| 4,492,909 | 1/1985 | Hartwig | 318/696 |
| 4,510,266 | 4/1985 | Eertink | 318/696 |
| 4,587,473 | 5/1986 | Turvey | 318/696 |
| 4,678,979 | 7/1987 | Hori | 318/696 |

(List continued on next page.)

OTHER PUBLICATIONS

SGS–Thomson Microelectronics L6219 Stepper Motor Driver datasheet–Dec. 1996.

SGS–Thomson Microelectronic PBL3717A Stepper Motor Driver datasheet–Apr. 1993.

Allegro MicroSystems, Inc. 3955 Full–Bridge PWM Microstepping Motor Driver datasheet–1997.

SGS–Thomson Microelectronics Power Controllers and Motor Drivers Short Form Catalog (pg. 24)–Nov. 1994.

*Primary Examiner*—Robert E. Nappi
*Assistant Examiner*—Rina I. Duda
(74) *Attorney, Agent, or Firm*—Beth A. Vrioni; Brian R. Woodwooth

(57) ABSTRACT

A stepper motor controller and method for controlling the motion of a stepper motor by selectively energizing the motor's windings so that the current level in the windings match a desired current profile. The motor controller comprises a master logic device, preferably a microprocessor or microcontroller, which is programmed with logic for issuing control signals corresponding to the sequence with which the windings of the stepper motor are energized and the desired current profile. A portion of the control signals are received by a slaved logic device, which is programmed with logic for generating ramp command signals corresponding to the desired current profile. The slaved logic device produces a ramp command signal that is received by a digital potentiometer, which preferably includes an up/down counter. The output signal produced by the digital potentiometer corresponds to a current count value of the up/down counter, and it is controlled by the ramp command signals. By controlling the digital potentiometer with the ramp command signals, a current command signal is produced corresponding to the desired current profile and having a range between low and high reference voltages. This current command signal is provided to a stepper motor drive circuit, which controls the current levels in the stepper motor windings so that they correspond to the desired current profile and are phased according to required sequence.

31 Claims, 13 Drawing Sheets

U.S. PATENT DOCUMENTS

| | | | |
|---|---|---|---|
| 4,718,576 | 1/1988 | Tamura et al. | 222/63 |
| 4,737,711 | 4/1988 | Doelves | 318/696 |
| 4,739,346 | 4/1988 | Buckley | 346/138 |
| 4,751,445 | 6/1988 | Sakai | 318/696 |
| 5,055,761 | 10/1991 | Mills | 318/696 |
| 5,084,663 | 1/1992 | Olsson | 318/701 |
| 5,125,499 * | 6/1992 | Saathoff et al. | 198/468.01 |
| 5,194,796 | 3/1993 | Domeki et al. | 318/696 |
| 5,274,316 | 12/1993 | Evans et al. | 318/696 |
| 5,283,510 | 2/1994 | Tamaki et al. | 318/696 |
| 5,418,443 | 5/1995 | Kikuchi | 318/807 |
| 5,428,284 | 6/1995 | Kaneda et al. | 318/778 |
| 5,563,486 | 10/1996 | Yamamoto et al. | 318/696 |
| 5,572,105 | 11/1996 | Nojima et al. | 318/696 |
| 5,627,443 | 5/1997 | Kimura et al. | 318/696 |
| 5,640,075 | 6/1997 | Brasseur et al. | 318/685 |
| 5,648,710 | 7/1997 | Ikeda | 318/685 |
| 5,659,234 | 8/1997 | Cresens | 318/696 |
| 5,744,929 | 4/1998 | Miyazaki | 318/696 |
| 5,841,261 * | 11/1998 | Nojima et al. | 318/696 |
| 5,889,379 | 3/1999 | Yanagi et al. | 318/696 |
| 5,894,209 | 4/1999 | Takagi et al. | 318/696 |
| 5,923,159 * | 7/1999 | Ezell | 323/354 |
| 5,932,987 * | 8/1999 | Mcloughlin | 318/696 |

* cited by examiner

| PRESENT STATE | | | INPUTS | | | NEXT STATE | | | OUTPUTS | | | | NEXT STATE SETUP LOGIC 8:1 MUX OUTPUTS WHEN SELECT = PRESENT STATE | | |
|---|---|---|---|---|---|---|---|---|---|---|---|---|---|---|---|
| Y1 | Y2 | Y3 | X1 | X2 | X3 | Y1+ | Y2+ | Y3+ | Z1 | Z2 | Z3 | Z4 | DY1 | DY2 | DY3 |
| 0 | 0 | 0 | 0 | - | - | 0 | 0 | 0 | 0 | X2 | 0 | - | 0 | 0 | X1 |
| 0 | 0 | 0 | 1 | - | - | 0 | 0 | 0 | 1 | X2 | 0 | - | | | |
| 0 | 0 | 1 | 0 | 0 | - | 0 | 0 | 1 | 1 | | 1 | 1 | X1' | X1 X3 | X2' + X1 X3' |
| 0 | 0 | 1 | 0 | 1 | - | 1 | 0 | 0 | 1 | | 1 | 1 | | | |
| 0 | 0 | 1 | 1 | 0 | 0 | 0 | 1 | 1 | 1 | | 1 | 1 | | | |
| 0 | 0 | 1 | 1 | 0 | 1 | 1 | 1 | 0 | 1 | | 1 | 1 | | | |
| 0 | 0 | 1 | 1 | 1 | 0 | 0 | 1 | 1 | 1 | | 1 | 1 | | | |
| 0 | 0 | 1 | 1 | 1 | 1 | 0 | 0 | 0 | 1 | | 1 | 1 | | | |
| 0 | 1 | 0 | 0 | 0 | - | 1 | 0 | 0 | 1 | 1 | 0 | - | X1' + X2' | X1 X2 | 0 |
| 0 | 1 | 0 | 0 | 1 | - | 0 | 1 | 0 | 1 | 1 | 0 | - | | | |
| 0 | 1 | 0 | 1 | 0 | - | 1 | 0 | 1 | 1 | 1 | 0 | - | | | |
| 0 | 1 | 0 | 1 | 1 | - | 1 | 1 | 0 | 1 | 1 | 0 | - | | | |
| 0 | 1 | 1 | 0 | 0 | - | 1 | 0 | 1 | 1 | 0 | 0 | - | X1' + X2 | X1 X2' | 1 |
| 0 | 1 | 1 | 0 | 1 | - | 0 | 1 | 1 | 1 | 0 | 0 | - | | | |
| 0 | 1 | 1 | 1 | 0 | - | 1 | 1 | 1 | 1 | 0 | 0 | - | | | |
| 0 | 1 | 1 | 1 | 1 | - | 1 | 0 | 1 | 1 | 0 | 0 | - | | | |
| 1 | 0 | 0 | - | - | - | 1 | 1 | 1 | 1 | 1 | 1 | 0 | 1 | X3 | 0 |
| 1 | 0 | 1 | - | - | - | 0 | 1 | 0 | 1 | 0 | 1 | 0 | 1 | X3 | 1 |
| 1 | 1 | 0 | 0 | - | - | 0 | 0 | 0 | 1 | 1 | 0 | - | X1 X2 | X1 X2 | X1 X2' |
| 1 | 1 | 0 | 1 | 0 | - | 0 | 0 | 1 | 1 | 1 | 0 | - | | | |
| 1 | 1 | 0 | 1 | 1 | - | 1 | 1 | 0 | 1 | 1 | 0 | - | | | |
| 1 | 1 | 1 | 0 | - | - | 0 | 1 | 0 | 1 | 0 | 0 | - | X1 X2' | X1 X2' | X1 |
| 1 | 1 | 1 | 1 | 0 | - | 0 | 0 | 1 | 1 | 0 | 0 | - | | | |
| 1 | 1 | 1 | 1 | 1 | - | 1 | 1 | 1 | 1 | 0 | 0 | - | | | |

*FIG. 8*

| |
|---|
| Z1 = Y1 + Y2 + Y3 |
| Z2 = Y2·Y3' + Y1·Y2'·Y3' + X2·Y1'·Y2' |
| Z3 = Y1·Y2' + Y2'·Y3 |
| Z4 = Y1'·Y2·Y3 |

USE OF DIGITAL CURRENT RAMPING TO REDUCE AUDIBLE NOISE IN STEPPER MOTOR

FIELD OF THE INVENTION

This invention generally relates to a power source for a stepper motor, and more specifically, to a stepper motor having a power source that is digitally controlled to limit a slope of the power signal applied to the stepper motor.

BACKGROUND OF THE INVENTION

Stepper motors are well known in the art and are used in a wide variety of devices, including printers, disk drives, and other devices requiring precise positioning of an element. Stepper motors provide many advantages over other types of motors, most notably the ability to rotate through controlled angles of rotation, called steps, based on command pulses from a driver circuit. The accuracy of the stepped motion produced by a stepper motor is generally very good, since there is not a cumulative error from one step to another. The ability to incrementally rotate a shaft through a defined number of fixed steps enables stepper motors to be used with open-loop control schemes (i.e., applications in which a position feedback device such as an optical encoder or resolver is unnecessary), thereby simplifying the motion control system and reducing costs.

The speed of stepping motors can be readily controlled based on the pulse frequency employed, enabling stepping motors to achieve variable speed synchronous movement of a load that is directly coupled to the drive shaft of the motor. Furthermore, stepper motors are reliable, since they do not include contact brushes that can wear out. Typically, the only parts in a stepper motor susceptible to wear are the motor bearings.

Stepper motors generally have two phases, but three, four and five-phase motors also exist. FIG. 1 shows a typical two-phase motor, comprising a stator A and a stator B, each of which produce a magnetic flux with opposite poles at end faces 300 when a respective phase A winding 302 and phase B winding 304 are energized with an electric current. The direction of the magnetic flux is determinable by applying the "right-hand rule." In FIG. 1, a current $I_B$ flows through the phase B windings, creating a magnetic flux in stator B, as indicated by the directions of the arrows. This flux produces a torque applied to the rotor, causing the rotor to turn so that the magnetic field produced by the poles in the rotor are aligned with the magnetic field produced by stators A and B. In this case, the rotor will rotate clockwise so that its south pole aligns with the north pole of stator B at a position 2, and its north pole aligns with the south pole of stator B at a position 6. To continually rotate the rotor, current is applied to the phase A and phase B windings in a predetermined sequence, producing a rotating magnetic flux field.

Stepper motors are typically positioned by a sequence of command pulses that are received by a drive circuit portion of a stepper motor driver, which produces outputs signals to drive the stator windings (i.e., "coils" in the motor). This sequence of command pulses corresponds to one of the four drive modes that are typically used to move and position stepper motors, including the wave drive (one phase on), full-step drive (two phases on), half-step drive (one and two phases on), and microstepping (continuously varying phase currents). The following discussion of these various drive modes are made with reference to FIGS. 2A–2B and 3A–3B.

FIG. 3A shows a typical six-wire unipolar drive circuit. In order to drive a unipolar stepper motor, it is necessary to energize the windings of the motor in a predetermined sequence. This procedure can be accomplished through the use of four switches 50, 52, 54, and 56 (e.g., Darlington pair switches or field-effect transistors), each of which is connected to ground at one terminal, and connected to a respective winding at the other terminal. A positive supply voltage is provided at common or center taps 58 and 60. Current can be caused to flow through windings corresponding to motor phases A, $\overline{A}$, B, and $\overline{B}$ by respectively closing switches 50, 52, 54, and 56, each of which provides a path to ground through their corresponding winding. When current flows through the windings, a magnetic field is generated in accord with the right-hand rule, as discussed above, which causes the motor rotor to rotate so that it is aligned with the magnetic fields generated by stators A and B.

A somewhat more complex scheme is used for driving a bipolar motor. As shown in FIG. 3B, a typical bipolar drive circuit comprises a pair of H-bridge circuits, one for each winding. Each of the H-bridge circuits comprises four switches 62, 64, 66, and 68. The branches at the top of the bridges are connected to a positive supply voltage, while the branches at the bottom of the bridges are connected to ground. By selectively closing the H-bridge switches, current can be caused to flow through windings 70 and 72 in a desired direction, thereby producing motor phases A, $\overline{A}$, B, and $\overline{B}$. For example, to produce a current flow in winding 70 from right to left (i.e., motor phase A), switches 64 and 66 are closed, while switches 62 and 68 are kept open.

In a wave drive for a stepper motor, only one winding is energized at any given time. The windings on the stators are energized according to the sequence A→B→$\overline{A}$→$\overline{B}$, causing the rotor to step through positions 8→2→4→6. For unipolar and bipolar wound motors with the same winding parameters, this excitation mode will result in the same mechanical position of the rotor. The disadvantage of this drive mode is that in a unipolar wound motor, only 25% of the total motor winding is energized at any given time, and in a bipolar motor, only 50% of the total motor winding is used. Thus, the maximum potential torque output of the motor is not realized.

In a full-step drive for a stepper motor, two phases are energized at any given time. The windings on the stators are energized according to the sequence AB→$\overline{A}$B→$\overline{A}$ $\overline{B}$→A$\overline{B}$, causing the rotor to step through positions 1→3→5→7. When using the full-step mode, the angular movement will be the same as was discussed above for a wave drive, but the mechanical position is offset by one-half step. The torque output of a unipolar wound motor when using full-stepping is lower than for a bipolar motor (i.e., for motors with the same winding parameters), since the unipolar motor uses only 50% of the available winding, while the bipolar motor uses the entire winding.

The half-step drive mode combines both wave and full-step (one and two phases on) drive modes. As shown in TABLE 1 (below), the number of phases that are energized alternates between one and two phases during every other step. The windings on the stators are energized according to the sequence AB→B→$\overline{A}$B→$\overline{A}$→$\overline{A}$ $\overline{B}$→$\overline{B}$→A$\overline{B}$→A, causing the rotor to step through positions 1→2→3→4→5→6→7→8. This procedure results in angular movements that are half of those discussed above for wave and full-step drive modes. Half-stepping can reduce a phenomena referred to as resonance, which sometimes occurs when using the wave or full-step drive modes at certain step rates.

TABLE 1

| Phase | Wave Drive | | | | Normal Full-Step Drive | | | | Half-step Drive | | | | | | | |
|---|---|---|---|---|---|---|---|---|---|---|---|---|---|---|---|---|
| | 1 | 2 | 3 | 4 | 1 | 2 | 3 | 4 | 1 | 2 | 3 | 4 | 5 | 6 | 7 | 8 |
| A | ● | | | | ● | | | ● | ● | | | | | | ● | ● |
| B | | ● | | | ● | ● | | | | ● | ● | ● | | | | |
| $\overline{A}$ | | | ● | | | ● | ● | | | | ● | ● | ● | | | |
| $\overline{B}$ | | | | ● | | | ● | ● | | | | | ● | ● | ● | |

Resonance can be observed as a sudden loss or drop in torque at certain speeds, which can result in missed steps or loss of synchronism, and creates undesired noise and motor vibration. Resonance generally occurs when the input step pulse rate coincides with the natural frequency of a stepper motor, or multiples thereof. Often, there is a resonance area around the 100–200 pulse per second region and also, a resonance area toward the maximum stepping rate of the motor.

The natural frequency, $F_0$ (Hz), of a stepper motor is determined by the rotor and load inertia, $J_T = J_R + J_L$ (Kgm$^2$), holding torque, $T_H$ (Nm) (with the selected driving mode and current levels), and number of full-steps per revolution (n).

$$F_0 = (n \times T_H \div J_T)^{0.5} \div 4\pi \qquad (1)$$

If the motor damping is low, there is a clear risk of losing steps or generating noise when the motor is operated at or near the natural frequency. Depending on motor type, total inertia, and damping, this problem can also appear at or close to integer multiples and fractions of $F_0$, e.g., $F_0/4$, $F_0/3$, $F_0/2$, $2F_0$, $3F_0$, $4F_0$ etc. Normally, the frequencies closest to $F_0$ create the most problems.

When a non-microstepping driver is used, the main cause of these resonances is that the stator flux is moved in a discontinuous increment of 90 (full-step mode) or 45 (half-step mode) electrical degrees at a time. This movement exerts a pulsing torque on the rotor, which excites the resonance. The energy transferred to the rotor, when a single step is taken, is in the worst case (no load friction), equal to:

$$(4T_H \div n) \times [1 - \cos(f_e)] \qquad (2)$$

wherein $T_H$ and n are as above and $f_e$ is the electrical step angle, i.e., 90° for a full-step, 45° for a half-step. This equation shows that using half-steps instead of full-steps reduces the excitation energy to approximately 29% of the full-step energy. Furthermore, if the motor is microstepped using ⅟₃₂ steps, only 0.1% of the full-step energy is used.

From the foregoing, it will be apparent that there is a direct correlation between rotor torque discontinuities and resonance. Ideally, if a motor could be driven so as to produce a constant motor torque, there would be no resonance. In theory, it would be possible to provide a constant rotor torque in a two-phase stepper motor if the waveforms of the currents in the motor windings were two sinusoids, 90° out of phase (actual stepper motors approach, but do not produce this ideal result). A common way to produce winding currents that approach these ideal sinusoidal waveforms is to use microstepping, wherein the currents supplied to the motor windings are stepped in small increments to produce a pseudo-sinusoidal current waveform.

An inherent drawback to microstepping is that it generally requires relatively complex control circuitry to implement. In a typical microstepping driver, a dedicated logic circuit, e.g., a microprocessor, microcontroller, ASIC, or DSP, is used to provide control signals to a driver circuit, which provides current to the windings (i.e., phases) of the stepper motor in accord with a predetermined sequence. The current command control signals are generally in the form of a voltage level or a pulse-width modulated signal. A common way to implement the simulated sinusoidal waveform discussed above is for the microprocessor to provide a digital signal to a digital-to-analog converter (DAC) at fixed time intervals corresponding to the stepping rate of the motor. For example, if it is desired to step a motor at 200 (full) steps/sec, and the microstepping level is ⅟₃₂ of a step, then the microprocessor would have to provide an updated current command signal at a rate of 32*200=6400 times per second (every 156 μs). Thus, if it is desired to use the microprocessor for carrying out another task simultaneously, the other task would have to be interrupted 6400 times a second to service the motor control requirements. This problem becomes worse because it is usually desirable to drive a motor at a variety of different speeds, each of which correspond to a different update rate. As a result, the sharing of the microprocessor for other tasks is often impractical, and may be impossible if the other task or tasks have their own timing requirements that cannot readily be interrupted in this manner.

Another method for minimizing the effect of resonance is to drive a stepper motor with a trapezoidal signal. As discussed above, resonance and noise is primarily caused by discontinuities (i.e., step changes) in the current levels flowing through the motor windings, which cause the rotor to "jerk" as it is stepped. Since a trapezoidal signal is stepless, it contains no discontinuities, and therefore greatly reduces resonance and noise problems.

As with microstepping, motor controllers that implement trapezoidal drive schemes are often complex, requiring the use of dedicated circuitry and typically requiring substantial processing overhead to obtain the desired trapezoidal drive current waveforms. It would therefore be desirable to provide a trapezoidal drive scheme that requires a substantially reduced processor workload, while minimizing the effects of resonance and noise.

SUMMARY OF THE INVENTION

In accord with the present invention, a stepper motor controller and method is provided that addresses the foregoing limitations of the prior art, with emphasis on reducing the audible noise that is caused by resonance. The invention provides a stepper motor controller that operates under a plurality of control modes, including a control mode that generates phased trapezoidal winding current waveforms with precise rise and fall times, with greatly reduced processor overhead. The phased trapezoidal waveforms are timed relative to a stepper motor's phase sequence such that substantially zero current is produced when the motor windings are switched between energized and de-energized states, resulting in a smooth rotor rotation with minimal audible noise and resonance.

According to a first aspect of the invention, a stepper motor controller is provided for controlling the motion of a stepper motor by selectively energizing the motor's windings so that the current level in the windings matches a desired predetermined profile. The controller comprises a master logic device, preferably a microprocessor or microcontroller, which is programmed with logic for generating control signals corresponding to the phase sequence with which the stepper motor is energized, and the desired current profile. A portion of the control signals are received by a slaved logic device, which is programmed with logic for generating ramp command signals corresponding to the desired current profile. The slaved logic device produces a ramp command signal that is received by a digital potentiometer, which preferably includes an up/down counter, so that the position of the digital potentiometer's wiper corresponds to a current count value that is controlled by the ramp command signals. By programming the digital potentiometer with the ramp command signals, a current command signal is produced corresponding to the desired current profile and having a range between low and high reference voltages supplied to respective terminals on the digital potentiometer. This current command signal is then provided to a stepper motor drive circuit, which controls the current levels in the stepper motor windings so that they correspond to the desired current profile and the windings are energized according to the stepper motor's phase sequence.

According to a second aspect of the invention, the desired current profile comprises a trapezoidal waveform having a positive and negative portion separated by a substantially zero current crossover point. A timing relationship between the trapezoidal current command signal and the motor phase sequence is defined such that changes in the motor phase command signals occur at points coincident to a current crossover point. As a result, the current in the selectively energized windings is substantially zero immediately after the windings are switched between energized and de-energized states.

According to another aspect of the invention, the stepper motor drive circuit comprises a chopper drive that provides a modulated current control signal to control the current level in the motor windings. Preferably, the chopper drive comprises a peak-limited, constant off-time modulator circuit that modulates the current control signal based on the current command signal and a winding current sense feedback signal such that if the winding current exceeds the commanded current, the current to the winding is switched off for a predetermined time interval.

According to yet another aspect of the present invention, the slaved logic device, which preferably comprises a field-programmable gate array, is programmed with logic for implementing a plurality of states corresponding to respective portions of the trapezoidal waveform, collectively defined by a state diagram. As the state diagram is traversed, ramp command signals are generated to program the digital potentiometer so that a portion of the trapezoidal waveform corresponding to a current state is produced. For instance, if the current state corresponds to an upwardly-ramped portion of the trapezoidal waveform, the ramp command signals comprise an up signal and a pulse train that cause the digital potentiometer's output voltage to ramp from a minimum low reference value to a maximum high reference value, thereby producing a trapezoidal current command signal comprising a voltage following the upwardly-ramped portion of that signal. Further, the slaved logic device is programmed with logic for determining when the ramped position is reached, whereupon the present state is caused to advance to a new state corresponding to the next portion of the trapezoidal waveform. By implementing this scheme, the only external signals needed to advance through the states, and thereby produce ramp command signals corresponding to the desired trapezoidal waveform, are the motor phase command signals provided by the master logic device.

According to still another aspect of the invention, the stepper motor controller further comprises a programmable voltage source that is programmed by the master logic device to control the voltage reference supplied to the digital potentiometer. The programmable voltage source, which preferably comprises a DAC, enables a stepper motor to be stepped using either a quarter-step pseudo-sinusoidal drive mode, or a half-step pseudo-sinusoidal drive mode, wherein a pair of motor windings are simultaneously energized using phased current command signals. The half-step and quarter-step pseudo-sinusoidal drive modes are enabled by novel current command signal waveforms comprising a zero current portion, a first portion, and a maximum current portion. Preferably, the current command signal waveforms further comprise sloped portions connected between zero current portions and adjacent first step portions such that the current in the motor windings when switching from or to a zero current condition is substantially zero. In addition, a low-pass filter preferably is used to filter the output signal produced by the DAC such that the current command signal waveforms resemble a sequence of scalloped half-sinusoids connected by zero current portions.

In accord with a still further aspect of the present invention, a method is defined for controlling a stepper motor using the stepper motor controller, generally in the manner discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

Figure 6A:
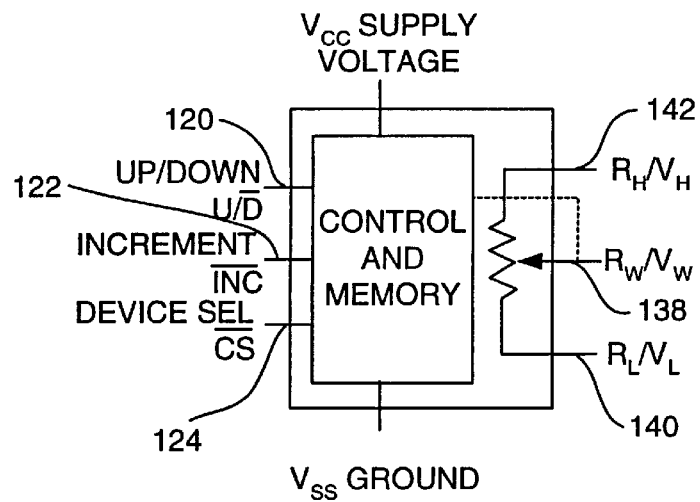
Figure 6B:
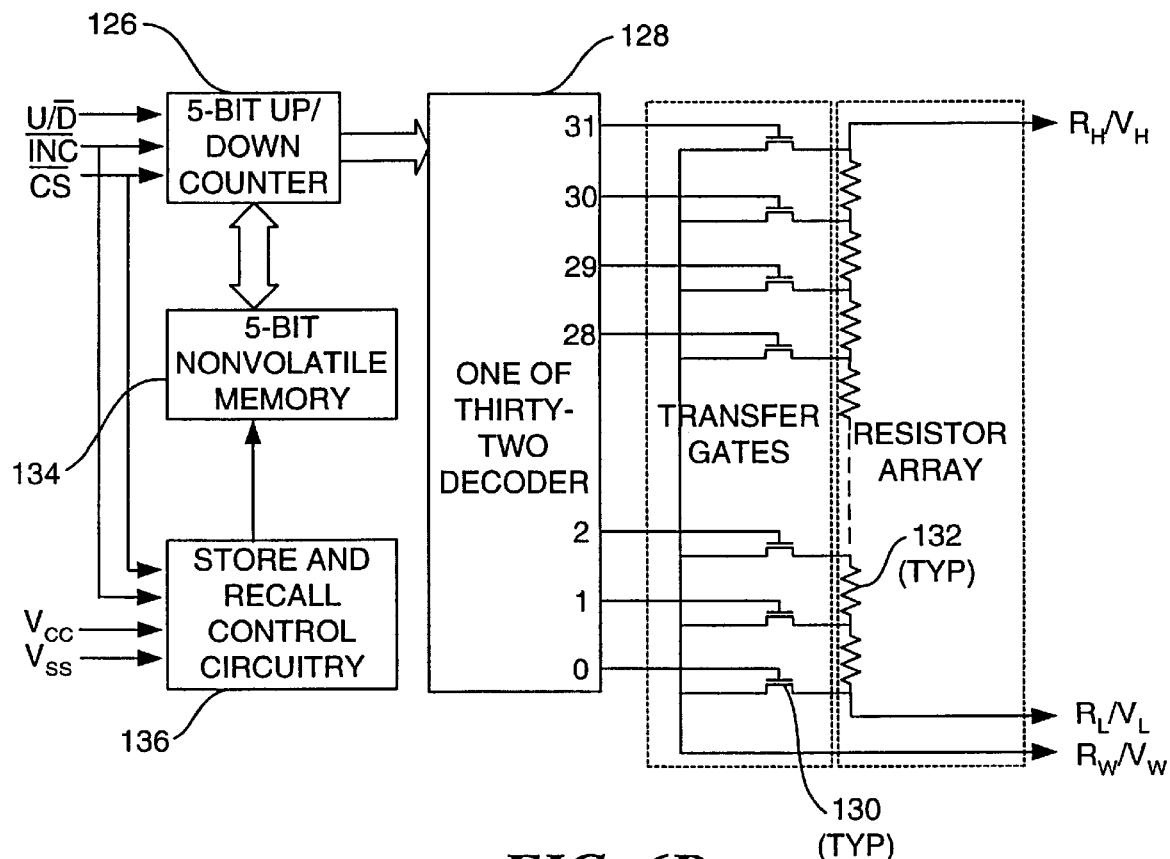
Figure 7:
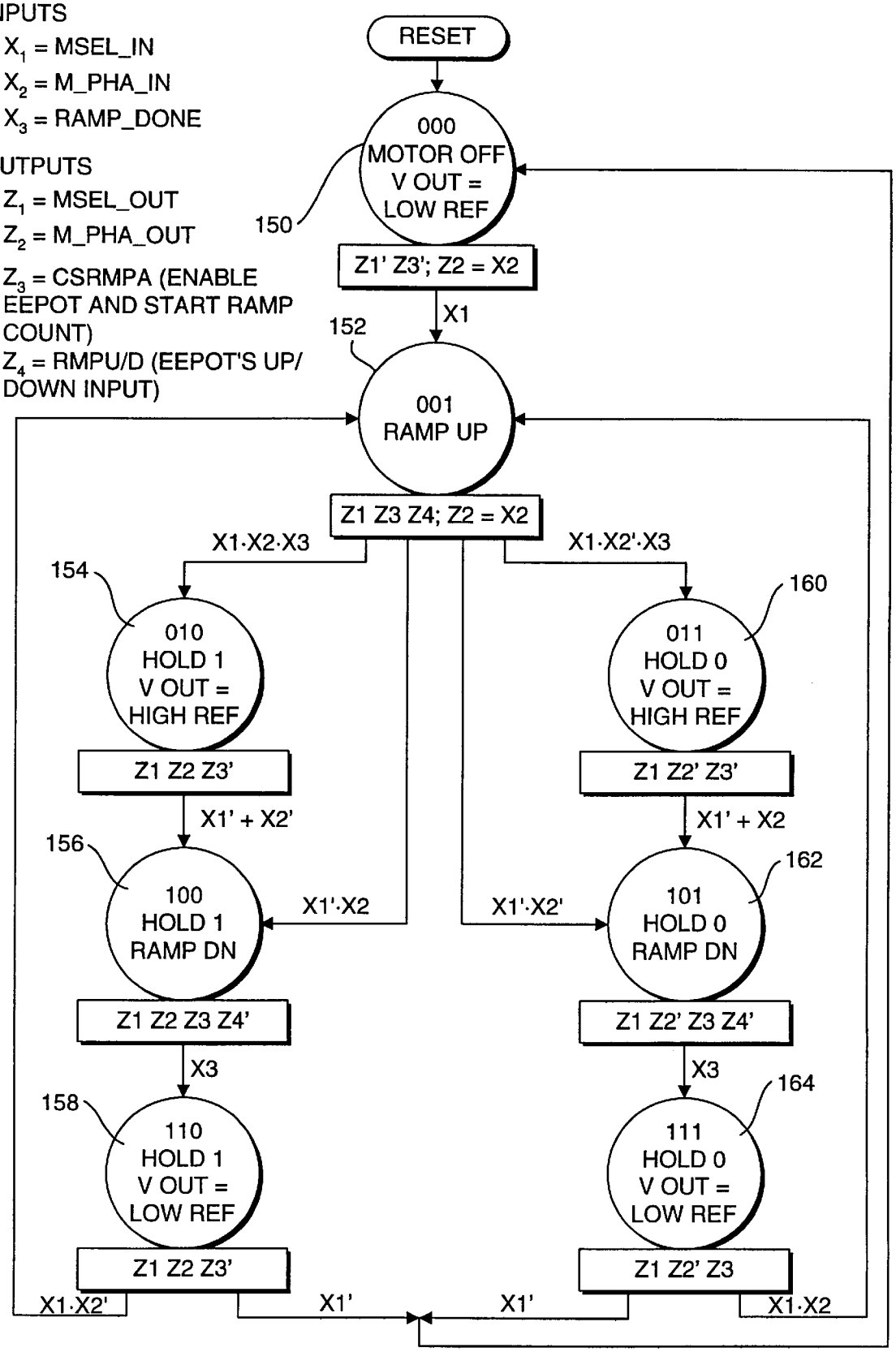
Figures 9, 10:
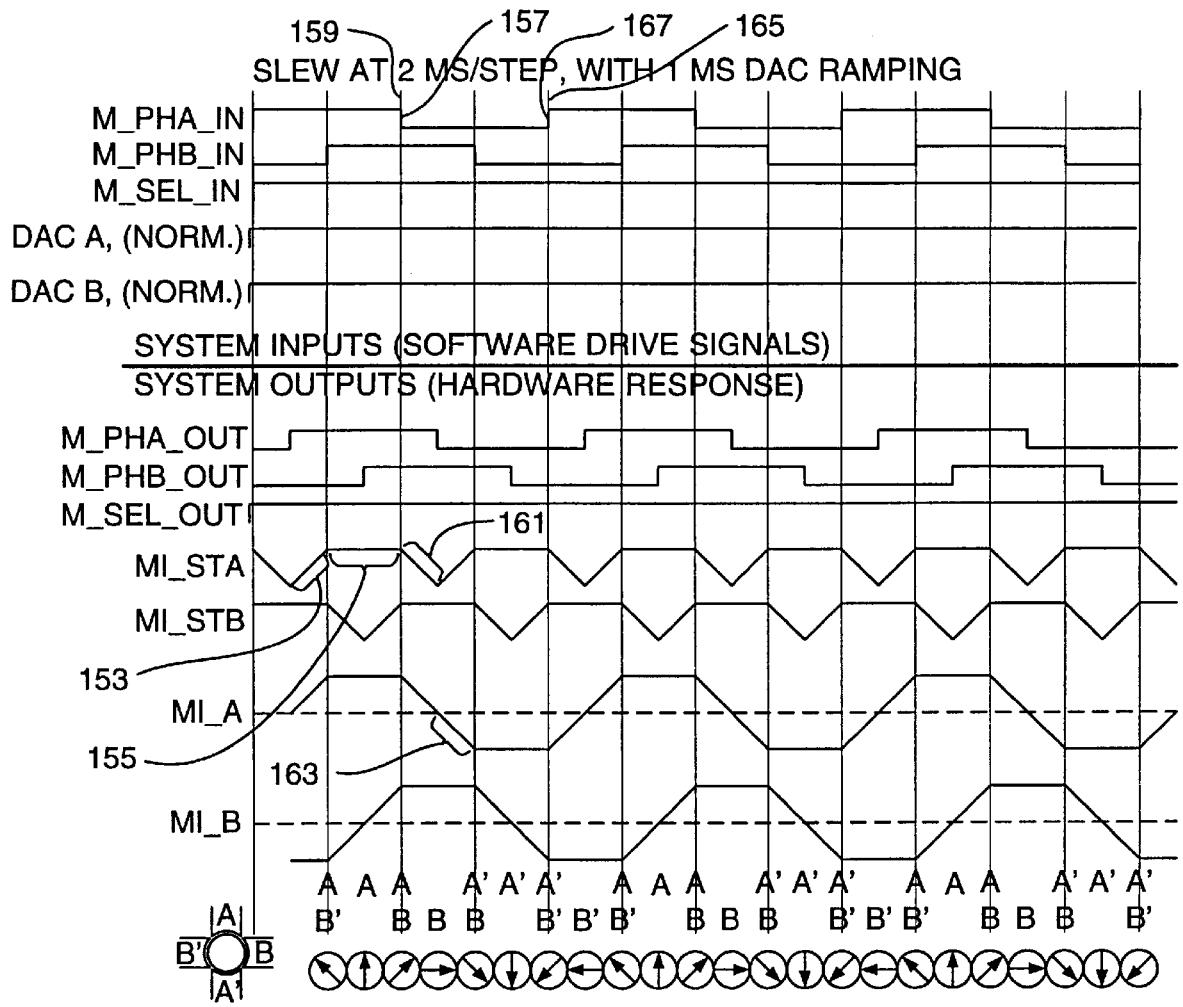
Figure 11:
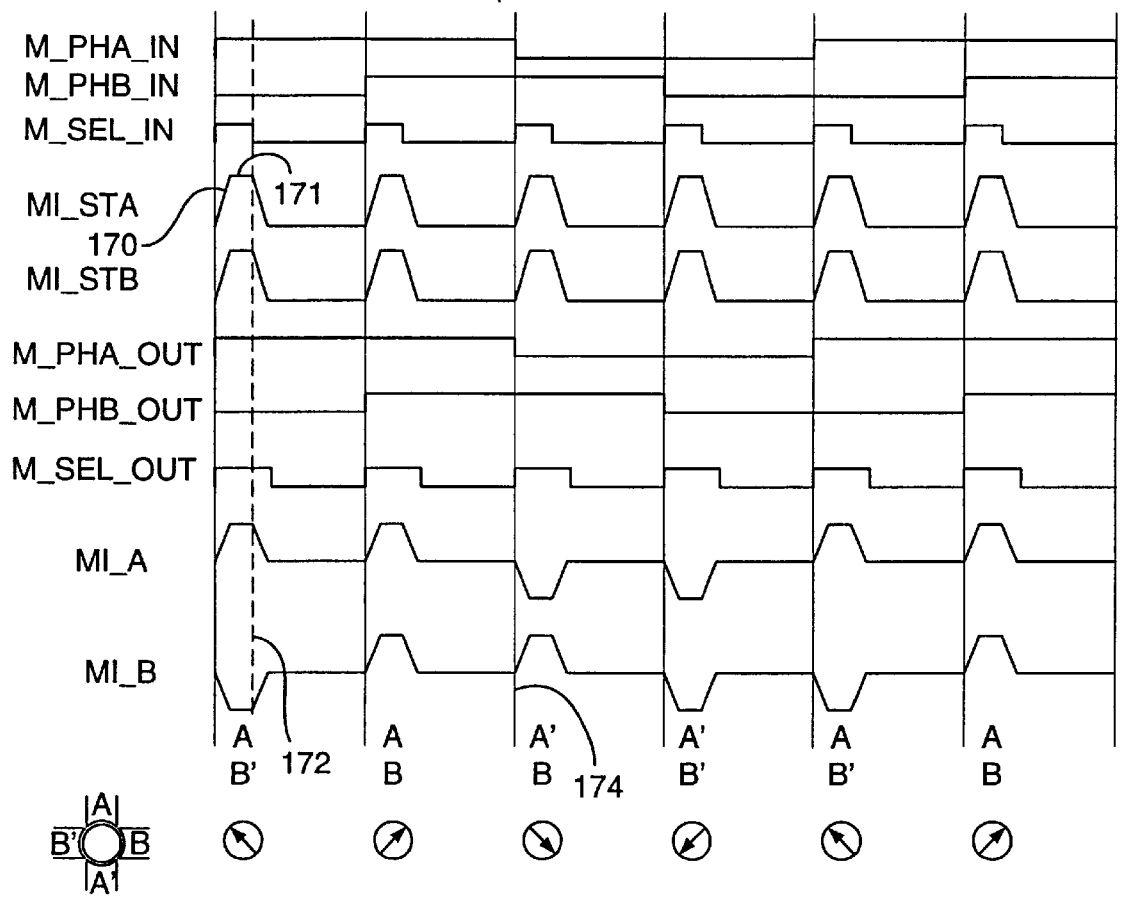
Figure 12:
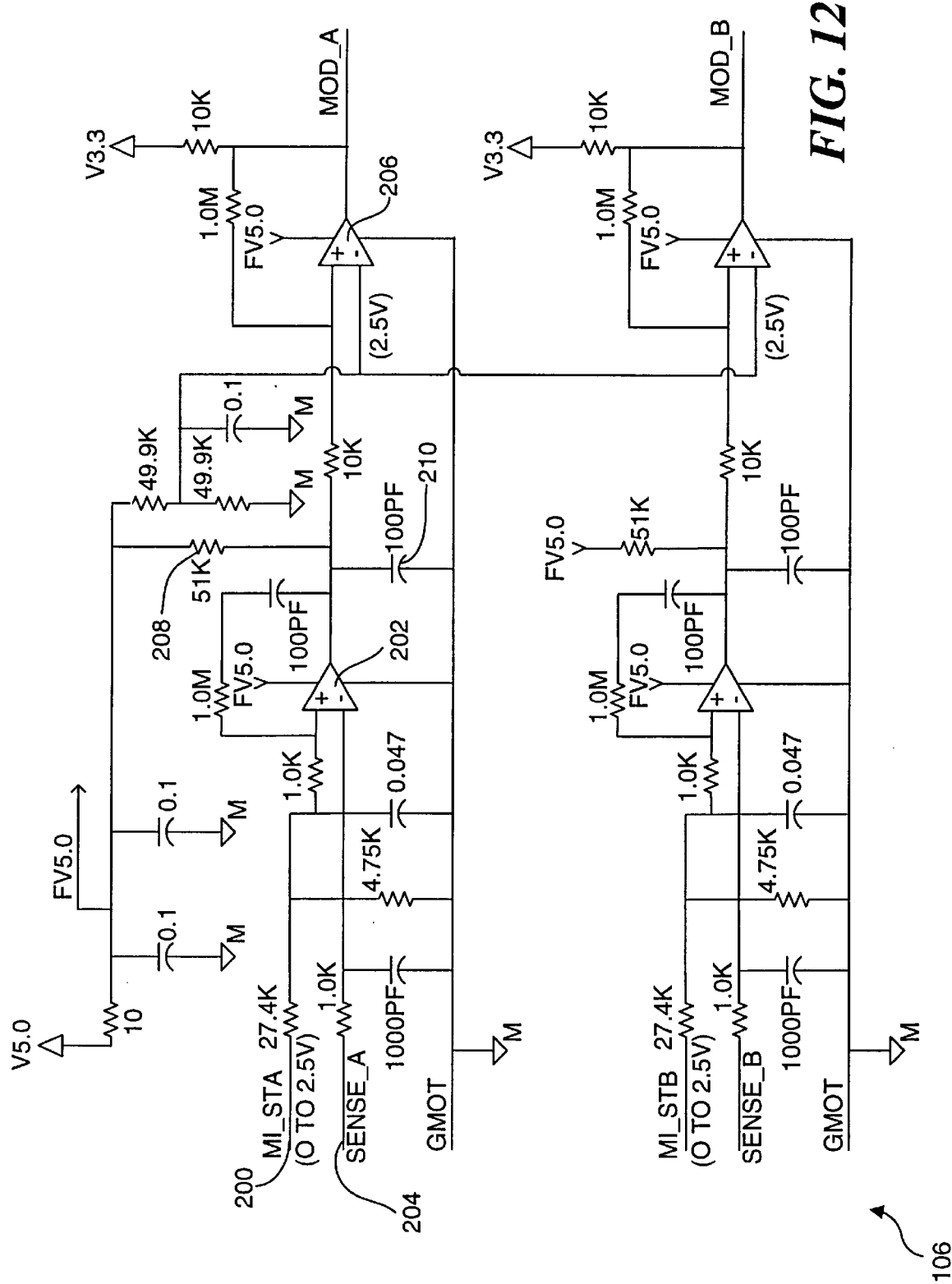
Figure 13:
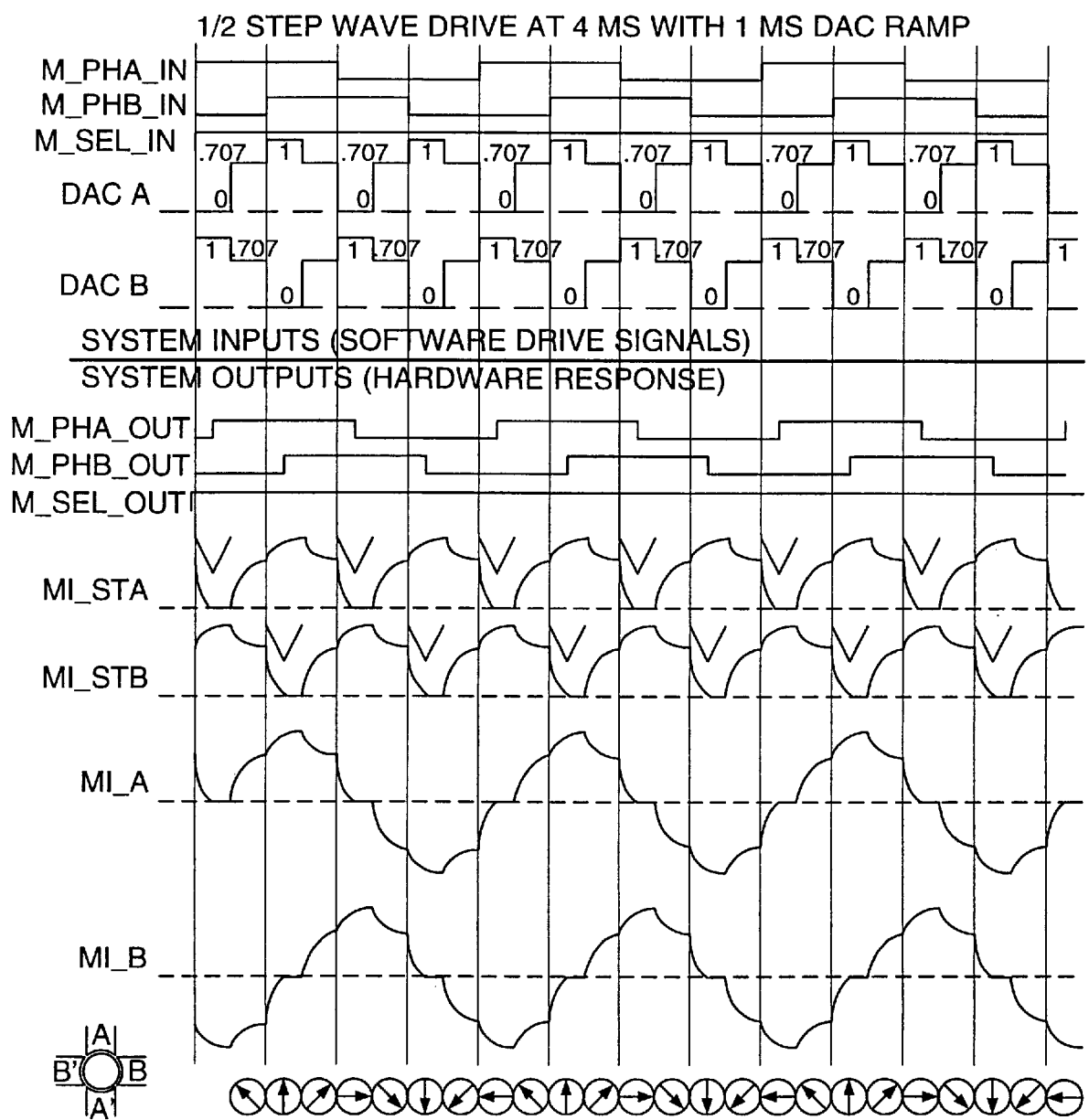
Figure 14:
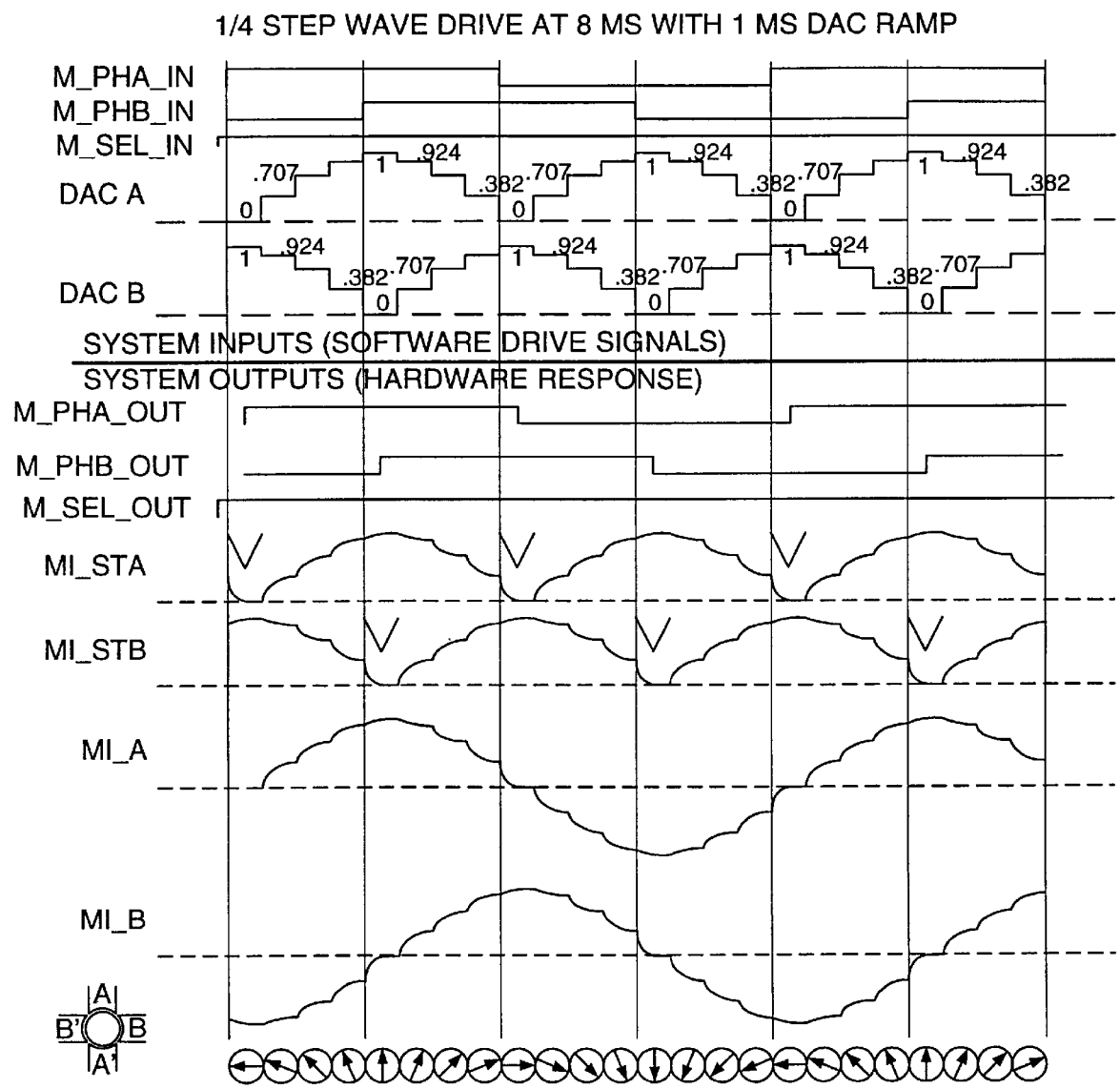
Figure 15:
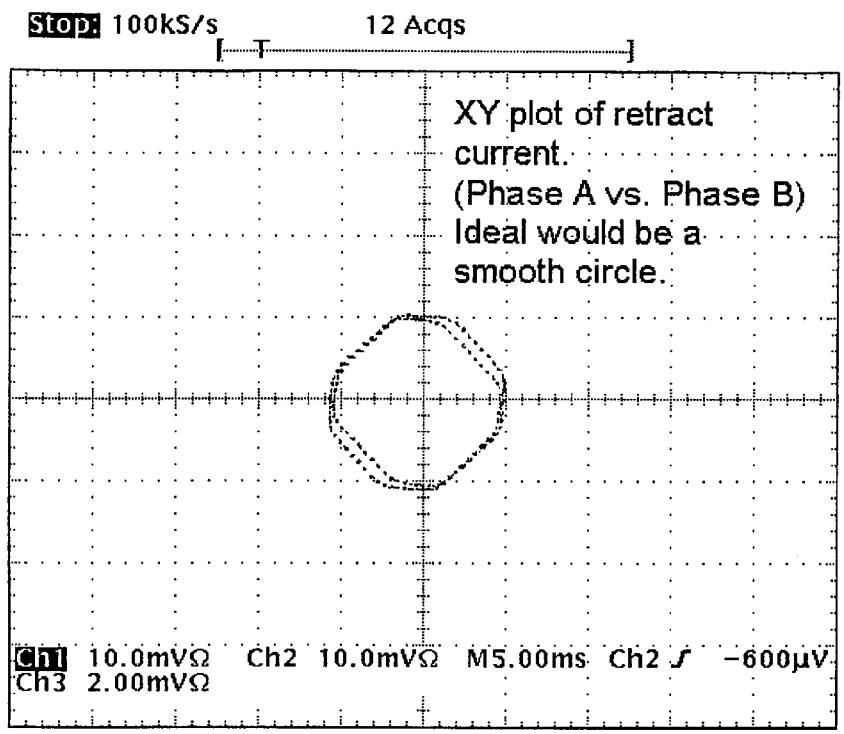
Figure 16:
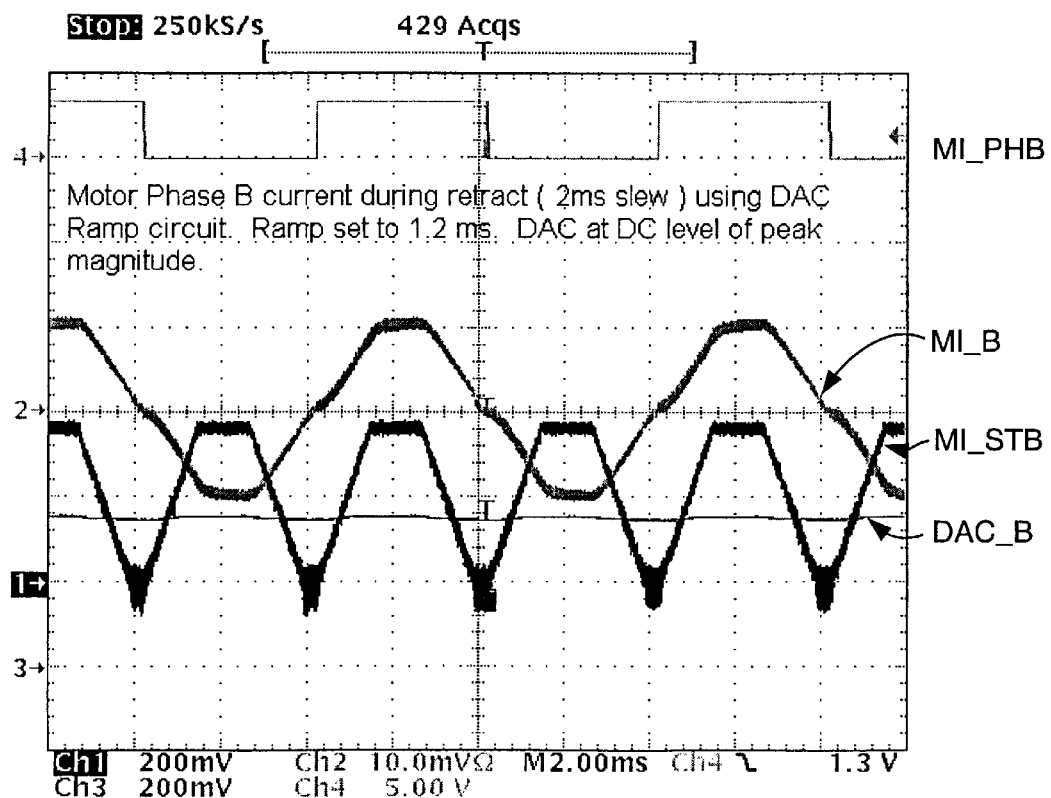

FIGS. 6A and 6B respectively show simplified and detailed circuit diagrams of the digital potentiometer employed by an embodiment of the present invention in generating a ramped current reference signal;

FIG. 7 is a state diagram corresponding to a trapezoidal drive scheme of the present invention;

FIG. 8 is a state table corresponding to the state diagram of FIG. 7;

FIG. 9 is a timing diagram corresponding to a trapezoidal drive scheme in which the drive signal applied to a stepper motor is stepped continuously at a rate of 2 ms/step;

FIG. 10 is a table comprising logical equations for determining the output values corresponding to the state diagram of FIG. 7;

FIG. 11 is a timing diagram corresponding to a full-stepping drive mode comprising a trapezoidal drive portion and a rest portion for each step;

FIG. 12 is a circuit diagram corresponding to a peak-limited, constant-time off modulator used in a preferred embodiment of the present invention to control winding current levels;

FIG. 13 is a timing diagram corresponding to a one-half step wave drive mode at a rate of 4 ms/step;

FIG. 14 is a timing diagram corresponding to a one-fourth step wave drive mode at a rate of 8 ms/step;

FIG. 15 is an X-Y plot produced during experimental testing of the present invention that illustrates the current motor phases A vs. B when operating the stepper motor controller in the trapezoidal drive mode; and FIG. 16 is an Y-T plot produced during experimental testing of the present invention that illustrates the input control signals and output current levels produced when operating the stepper motor controller in the trapezoidal drive mode.

DESCRIPTION OF THE PREFERRED EMBODIMENT

The present invention provides a novel digital current ramping source that produces a trapezoidal drive signal used to control current levels in a stepper motor winding so that noise and resonance effects are minimized, and so that the digital current ramping source requires minimal microprocessor input or overhead. The invention is described below with reference to a medical application in which it is used with a cassette infusion pump. It will be recognized by those skilled in the art that the digital current ramping source in accord with the present invention is not limited in application to the specific uses described herein, but instead, may be applied to a stepper motor in almost any application.

Figure 1:
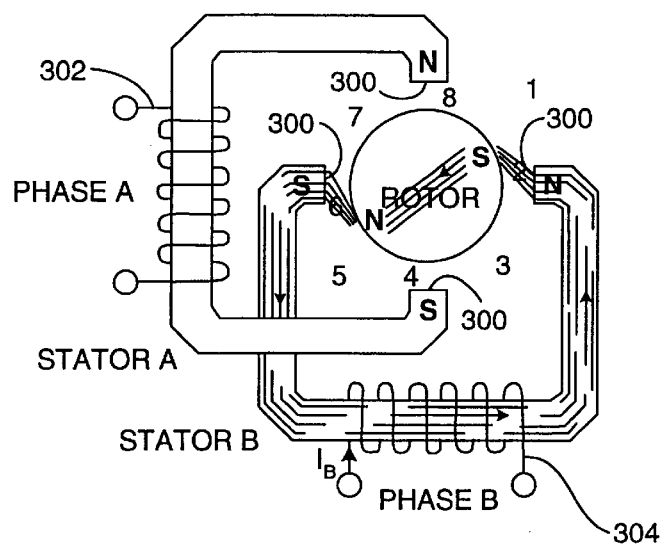
FIG. 1 is a simplified schematic diagram of magnetic circuits employed in a bipolar stepper motor.
Figure 4:
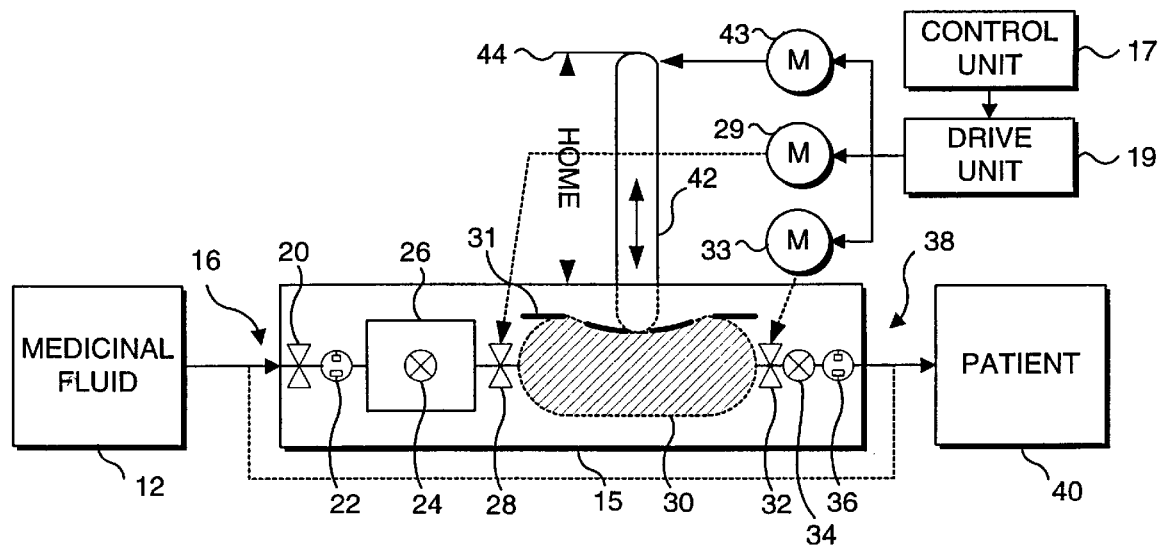
FIG. 4 is a schematic block diagram of a cassette-type infusion pump that includes a stepper motor, illustrating an exemplary application of the present invention.
Figure 2A:
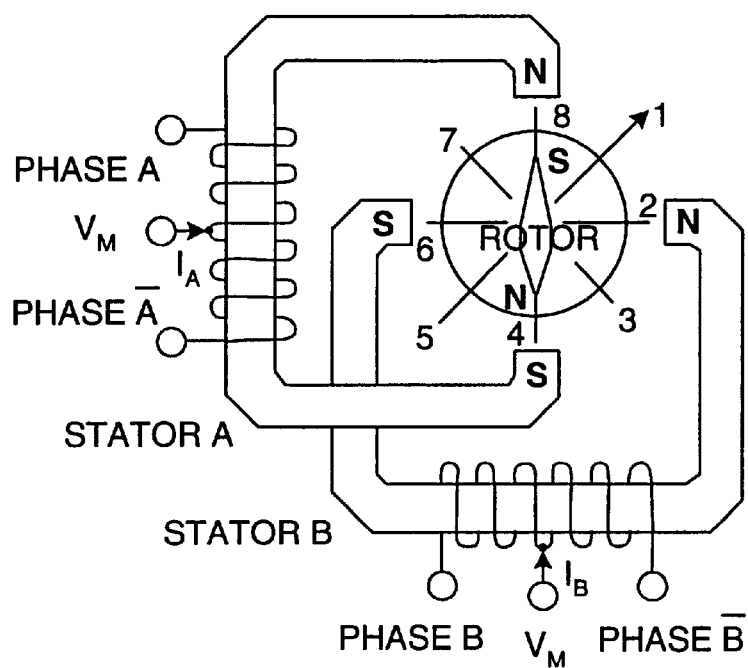
FIGS. 2A and 2B are simplified schematic diagrams respectively illustrating primary components of unipolar and bipolar stepper motors.
Figure 2B:
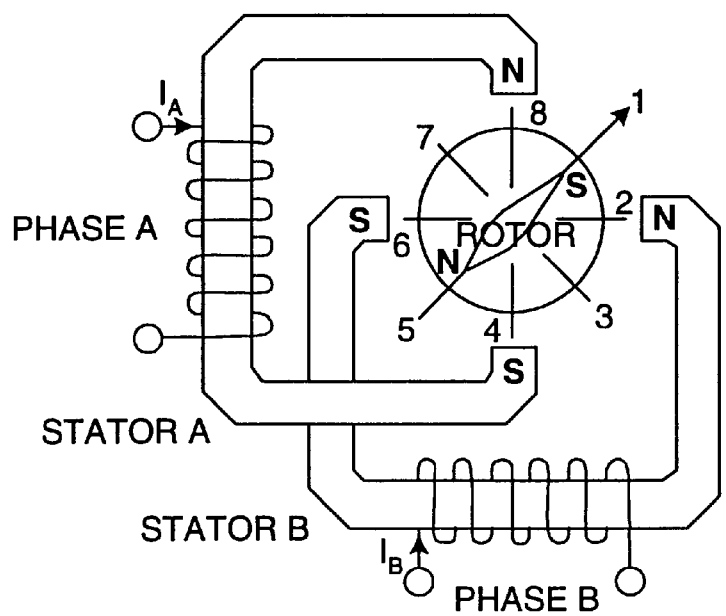

The cassette infusion pump discussed below is used for infusing medicinal fluid into a patient's body at very precise flow rates. The primary fluid delivery components of this system are shown in FIG. 4. In practice, the cassette infusion pump system employs a multi-channel pump cassette. However, for illustrative purposes, only a single channel pump cassette is shown in the Figure and described below. Further details of the cassette infusion pump are disclosed in a co-pending commonly assigned application, Ser. No. 09/464,812, filed Dec. 17, 1999, entitled "Compensation for Pressure Differences across Valves in Cassette Type IV Pump," the disclosure and drawings of which are hereby specifically incorporated herein by reference.

The process that the cassette infusion pump uses in delivering medicinal fluid to a patient is as follows. With reference to FIG. 4, a source 12 of medicinal fluid is coupled in fluid communication with a proximal end 16 of a cassette 15. The flow of medicinal fluid into the cassette is selectively controlled by a supply valve 20. After entering a passage in the cassette, the medicinal fluid flows through an air sensor 22 and into a mixing chamber 26. The purpose of the air sensor is to detect air bubbles that may be entrained in the medicinal fluid before the fluid is passed on into the pumping chamber and enters the patient's vascular system, since excess air bubbles entering a patient's bloodstream can cause an air embolism with potentially harmful consequences. A proximal (or inlet) pressure sensor 24 is disposed adjacent to mixing chamber 26. The medicinal fluid exits the mixing chamber through an inlet valve 28, when the inlet valve is in its open position, and flows into a pumping chamber 30.

One side of chamber 30 is covered with an elastomeric membrane 31. Medicinal fluid is forced from pumping chamber 30 (when the inlet valve 28 is closed, and an outlet valve 32 is opened), as a plunger 42 acts on the elastomeric valve, forcing the elastomeric membrane into the chamber to displace the fluid contained therein. This plunger action is facilitated by moving a linear drive mechanism, e.g., a lead screw or ball screw (not shown), with a 3.6° stepper motor 43. In one embodiment of the cassette pump, the plunger position is variable from −489 steps to +220 steps, where a home position is nominally defined to be at 0 steps. A nominal stroke distance for plunger 42 to deliver 333 µl of fluid is +169 steps.

When outlet valve 32 is in its open position, the medicinal fluid forced from the chamber flows past a distal pressure sensor 34, through a distal air sensor 36, and exits the cassette through a tube set, through which it is conveyed to a patient 40. The infusion pump also includes a control unit 17 for the stepper motor. Control unit 17 preferably includes a microprocessor and a memory (not separately shown in FIG. 4), which enable execution of a control algorithm for controlling the operation of the infusion pump to deliver the medicinal fluid as desired. The microprocessor controls the stepper motors to vary the plunger and valve positions, thereby enabling the plunger to force a desired amount of fluid from pumping chamber 30 at a desired rate. In addition, the microprocessor is responsible for controlling the overall operation of the infusion pump, including responding to user input and controlling a liquid crystal display (not shown).

In FIG. 4, plunger 42 is shown in a home position (at the 0 step position). This position corresponds to the initiation of a pump cycle. Note that plunger 42 is in contact with the elastomeric membrane of pumping chamber 30, causing a slight deflection of the membrane. At the beginning of a pump cycle, outlet valve 32 is closed, inlet valve 28 is open, supply valve 20 is in the open position, and pumping chamber 30 is filled with the appropriate amount of medicinal fluid.

The use of a stepper motor enables the infusion pump to provide a wide range of delivery rates, making the device especially well suited for use in administering fluids to pediatric patients at extremely low medicinal fluid delivery rates. For example, the cassette infusion pump can supply a controlled rate of medicinal fluid at rates as low as 100 µl/hr. This rate is achieved by stepping the stepper motor once approximately every 70 seconds, so that each step delivers 2 µl of medicinal fluid to the patient.

The heart of the invention is the control unit for the stepper motor. In the following discussion, the control unit is described with reference only to its circuit elements that are employed to control the plunger stepper motor. Although not shown, in a preferred form, the control unit also includes circuit elements for controlling stepper motors 29 and 33 (FIG. 4), which respectively control the position of inlet valve 28 and outlet valve 32. Most of the control circuitry is multiplexed between the three motors, only the drive transistors are unique for each motor.

Figure 3A:
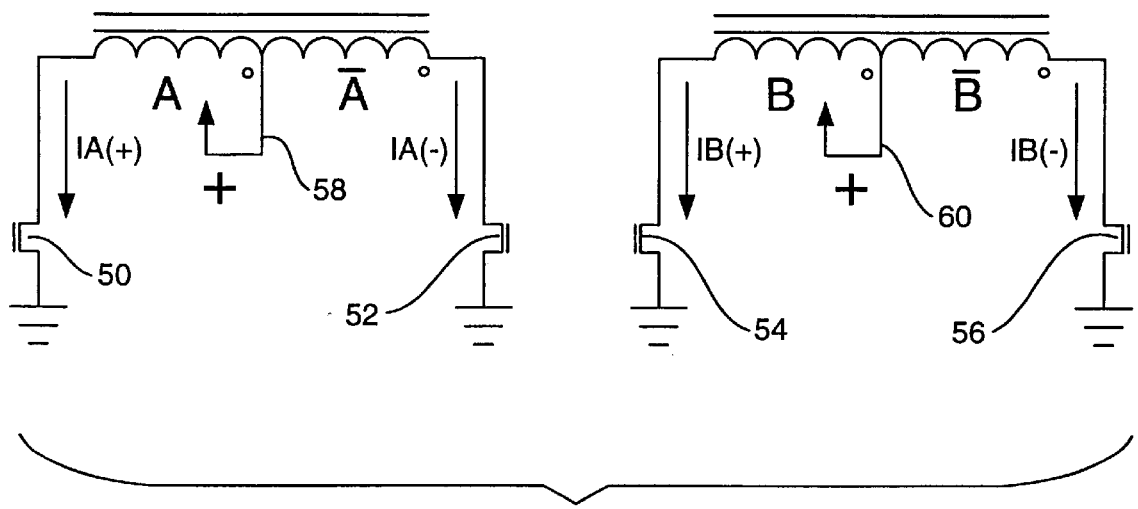
FIGS. 3A and 3B are schematic representations of the drive circuitry in unipolar and bipolar stepper motors.
Figure 3B:
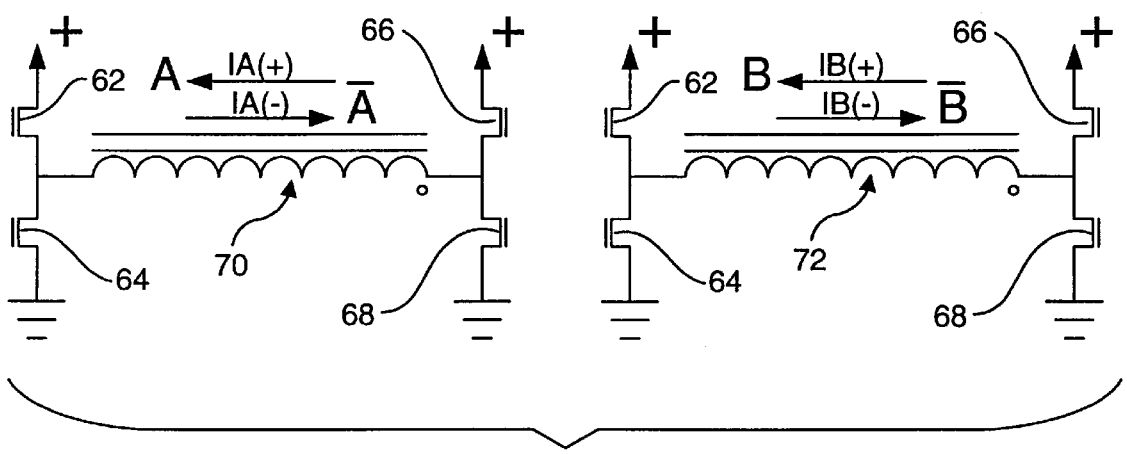
Figure 5:
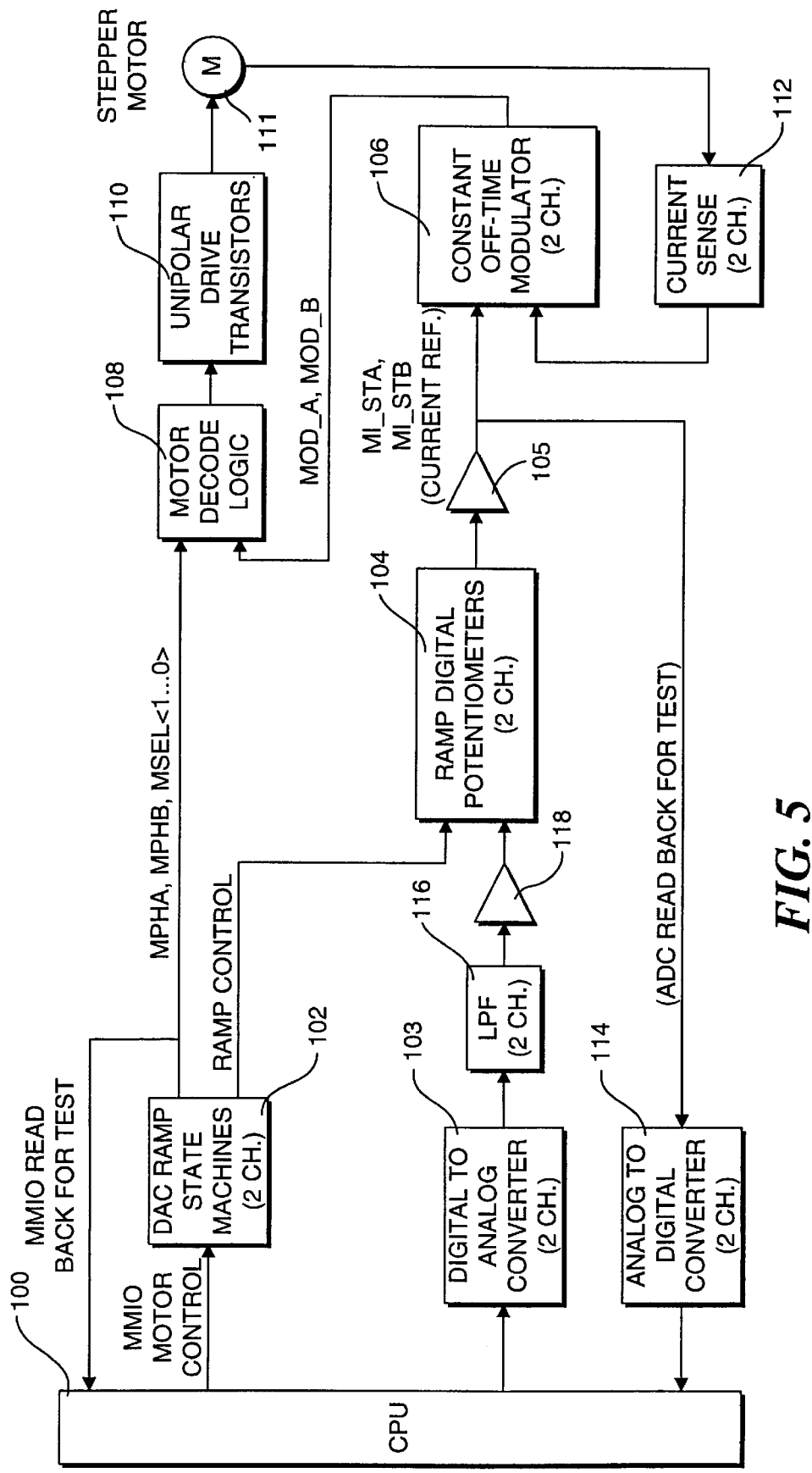
FIG. 5 is a schematic block diagram of an embodiment of the stepper motor controller of the present invention.

As shown in FIG. 5, the control unit includes a central processor unit (CPU) 100, which is a Motorola Corporation Model 68302 microprocessor in a preferred embodiment. The CPU is the master device for the control unit such that control of the stepper motor is entirely dependent on control signals issued by the CPU to other slaved components in the circuit. For instance, the CPU provides control signals to a two-channel state machine 102 and a two-channel DAC 103, which each provide a predetermined output based on the control signals they receive as inputs. The two-channel output signals for the state machine (corresponding to ramp command signals) and the two channel voltage output from the DAC are fed into a respective channels of a two-channel digital potentiometer 104, which produces current reference command signals for controlling the current level in the motor windings based on these inputs. The two current reference command signals are buffered by a pair of operational amplifiers (op amps) 105 of which only one is shown. The output signal from each op amp is received by a different channel of a two-channel peak-limited constant off-time modulator 106. Each channel of the peak-limited constant off-time modulator provides a peak-limited constant off-time modulated control signal that is used in energizing a respective winding in the stepper motor. Control signals from the state machine and the constant off-time modulator are received as inputs to a motor decode logic circuit 108, which produces output signals to control a plurality of unipolar drive transistors 110 connected to a unipolar stepper motor 111, substantially as shown in FIG. 3A and as described above. A current sense circuit 112 is employed for each channel to provide a feedback signal comprising a sensed current level in a corresponding winding for controlling the current levels in the motor windings. In addition, a two-channel analog-to-digital converter 114 is used for testing the current reference command signal produced by the two-channel digital potentiometer to ensure its accuracy.

The digital potentiometers are controlled by the state machine output so that the current reference command signal has a trapezoidal waveform, with the amplitude of the waveform being controlled by the output of the two-channel DAC. For illustrative purposes, the following discussion concerns the operation of only a single channel of the control unit. It will be understood that the same principles are applied to a second identical channel when the stepper motor is being operated. It should also be noted that although a digital potentiometer does not possess a mechanical wiper, it is common practice in the art to refer to a "wiper" in the digital potentiometer and to refer to the "position of the wiper" therein as determining an output voltage from the digital potentiometer, in a manner analogous to a conventional mechanical potentiometer.

The CPU provides an 8-bit digital input to DAC 103, which produces an analog output that is filtered by a low-pass filter 116, producing a signal that is buffered by an op amp 118. This signal is provided as a reference voltage to a "high reference voltage terminal" on the digital potentiometer. The digital potentiometer produces a signal on its wiper terminal having a voltage level corresponding to its wiper position, which varies between a low reference voltage (preferably a common ground to which the digital potentiometer's "low reference voltage terminal" is connected) and the DAC reference voltage, depending upon the position of the wiper relative to its minimum and maximum position, which respectively correspond to the low and high reference voltages. The digital potentiometer used in a preferred embodiment is a Xicor Corporation, Model X9313 digitally-controlled potentiometer (EEPOT).

With reference to FIGS. 6A and 6B, the digital potentiometer has three control inputs, including an up-down pin 120, an increment pin 122, and a device select pin 124. The digital potentiometer provides an internal 5-bit up-down counter 126, which provides input to a one of thirty two decoder 128 that controls operation of a plurality of transfer gates 130. The transfer gates are connected across a resistor array comprising a plurality of resistors 132. The up-down counter also transfers data to and receives data from a 5-bit non-volatile memory 134, which is controlled by a store and recall control circuit 136. The digital potentiometer produces an output voltage at a $R_W/V_W$ wiper terminal 138. By providing control signals to the digital potentiometer, the output voltage can be digitally ramped between a low reference voltage on a $R_L/V_L$ pin 140, preferably zero volts (i.e., ground), and the reference voltage output by the DAC, which is connected to a $R_H/V_H$ pin 142. This step is accomplished by providing an up or down control signal and providing a pulse train to the increment pin, which causes the wiper to move in $\frac{1}{32}$ increments of its full scale voltage ($R_H/V_H - R_L/V_L$) depending on the direction indicated by the logic level on the up-down pin.

The ramping of the output of the digital potentiometer is controlled by the state machine, based on input signals received from the CPU. The state machine controls the ramping so as to produce a trapezoidal current reference command signal by stepping through the state diagram shown in FIG. 7, which corresponds to the state table shown in FIG. 8. The state machine used in a preferred embodiment is a field-programmable gate array (FPGA), which is programmed to sequence through the state diagram based on input signals $X_1$, $X_2$, and $X_3$, as shown in the "INPUTS" column of FIG. 8.

The state machine provides four outputs, $Z_1$, $Z_2$, $Z_3$, and $Z_4$ (as shown in the "OUTPUTS" column of FIG. 8), based on the present state in the state diagram. These outputs are used to control switching of the stepper motor drive transistors and to control the output voltages produced by the digital potentiometers, wherein $Z_1$ corresponds to a motor select output signal MSEL_OUT, $Z_2$ corresponds to a motor phase output signal M_PHA_OUT, $Z_3$ corresponds to an enable digital potentiometer and initiate ramp count signal CSRMPA, and $Z_4$ corresponds to a digital potentiometer up/down input signal RMPU/D.

The state machine receives control input signals $X_1$ and $X_2$ from the CPU. $X_1$ and $X_2$ respectively correspond to a motor select input signal M_SEL_IN and a motor phase input signal M_PHA_IN, where these signals have the waveforms shown in the upper portion of the timing diagram of FIG. 9. In addition to signals $X_1$, and $X_2$, a third input signal, $X_3$, is internally generated by the state machine, such that this signal is switched from low-to-high upon completion of a ramping action, the details of which are discussed below.

The timing diagram in FIG. 9 corresponds to a drive mode in which the plunger stepper motor is stewed at a rate of 2 ms/step, using a 1 millisecond ramping, wherein each vertical timing mark represents a 2 ms time increment. (Please note that the actual time preferred time period is 1.56 ms—1 ms is used below for clarity). In this particular drive mode, the value of M_SEL_IN is always 1, while the motor phases A and B are 90° out of phase. In the following discussion, reference will primarily be made to the portion of the timing diagram that concerns the A-phase drive signals, which are processed by one of the two channels in the state machine. The processing of the signals corresponding to the B-phase of the motor is performed by an identical second channel of the control unit.

The output signals produced by the state machine and digital potentiometers are shown in the lower portion of the FIG. 9, where the output voltages produced at the digital potentiometers' wiper terminals (i.e., for the two channels) correspond to current reference command signals MI_STA (motor current set for stator A windings) and MI_STB (motor current setting for stator B windings), respectively. Note that the voltage of both the current reference command waveforms is always positive. In order to switch the polarity of the current in the windings, it is necessary to provide a motor phase signal that is used to provide appropriate switching of the transistors in the stepper motor drive circuit. As can be seen by the timing diagram, when the motor phase out signals (M_PHA_OUT and M_PHA_OUT) are high, the current in their associated winding has a positive value, while when the motor phase out signals are low, their associated winding currents have a negative value. Also note that there is a 1 ms lag between the motor phase input signals provided by the CPU and the motor phase output signal provided by the state machine; this delay is a result of the method used by the state machine to process the input command signals from the CPU.

A discussion of the state diagram now follows, with reference to FIGS. 7–9. Note that in FIGS. 7 and 8, as well as in the following description, an apostrophe (i.e., a "'") following a signal reference indicates that the signal is low, while the absence of an apostrophe indicates that a signal is high. Processing of the state diagram begins after a reset, whereupon the present state is initialized to a state 150 (FIG. 7), corresponding to present state values for $Y_1$, $Y_2$, and $Y_3$ of 000, respectively (see the "PRESENT STATE" column of the state table in FIG. 8). In state 150, the stepper motor is off (i.e., M_SEL_IN is low) and the digital potentiometer output is zero. In state 150, the outputs for $Z_1$ and $Z_3$ are 0's, the latter of which disables the input operation of the digital potentiometer, $Z_2=X_2$, and the value of $Z_4$ isn't considered. ($Z_4$ has no effect on the digital potentiometer, since the digital potentiometer is not enabled for receiving input.) The present state will remain in this initialized condition as long as the value of $X_1$ remains 0.

If the value of $X_1$ is switched to 1, indicating that the stepper motor has been selected to be move, the state is advanced to a state 152. State 152 corresponds to a ramp-up state during which the output of the digital potentiometer is ramped from zero volts up to the DAC reference voltage using a precise rise time based on a divided CPU clock signal. While in state 152, motor select signal $Z_1$ is 1, the motor phase output signal $Z_2$ corresponds to the motor phase input signal $X_2$, the digital potentiometer input enable and start ramp signal $Z_3$ is 1, and the up/down signal $Z_4$ is 1. Under these conditions, the current count of the up/down counter will increase by one (corresponding to a 1/32 incremental movement of the wiper) whenever the digital potentiometer receives a pulse on its increment pin. The ramping of the digital potentiometer output voltage is performed by providing a plurality of pulses at a fixed frequency to the increment pin, thereby incrementally moving the position of the wiper from its minimum position to its maximum position. The fixed-frequency pulses are provided by a divided CPU clock signal, which preferably is set to 23 kHz. This 23 kHz clock signal is also used to drive the state machine, and the inputs to the state machine are evaluated at every clock cycle. As shown in the corresponding timing diagram in FIG. 9, this ramped voltage output corresponds to an upwardly-ramped portion 153 of a trapezoidal current reference command signal MI_STA, which represents a desired current level when energizing a stepper motor's stator A windings.

As is shown by the MI_STA current reference command signal, the trapezoidal waveform transitions to a plateau portion 155 upon completion of upwardly-ramped portion 153. This plateau portion of the waveform has a corresponding state 154 in the state diagram, which is entered when $X_1 \cdot X_2 \cdot X_3$ is true (i.e., the logical value of $X_1$ ANDed with $X_2$ ANDed with $X_3$ equals a logic level one). This condition occurs when $X_3$ is switched to a logic level one and $X_2$ is equal to a logic level one (in this mode $X_1$ always remains at a logic level one). Recall that $X_3$ corresponds to the RAMP_DONE signal, indicating that the digital potentiometer has been ramped from either a minimum output voltage to a maximum output voltage or vice-versa. This signal is internally generated by the state machine in the following manner. The FPGA is programmed with logic for implementing an 8-bit synchronous up counter (not shown), which is preloaded with an initial count of 27, and has a clock input pin connected to the 23 kHz clock signal. When $Z_3$ goes high, the 8-bit up/down counter is enabled, and it begins to count from 27 until it reaches its maximum count of 64. This time period corresponds to 36 clock pulses, which are concurrently received by the 5-bit up/down counter of the digital potentiometer, thereby guaranteeing that the digital potentiometer has been ramped to its maximum position. At this point, the 8-bit synchronous up counter produces an overflow signal that sets input $X_3$ to logic level one. This step causes a transition to state 154, whereupon the output $Z_3$ becomes low, thereby disabling the digital potentiometer from receiving an input. As a result, the output voltage of the digital potentiometer remains equal to the DAC reference voltage.

The "HOLD 1" indication in state 154 (FIG. 7) concerns the direction of the current flow in the motor winding, where "HOLD 1" indicates flow in a positive direction, and "HOLD 0" indicates flow in a negative (i.e., reverse) direction. For example, waveforms MI_A and MI_B in FIG. 9 respectively correspond to the resultant currents flowing through the stator A and stator B windings, and the positive portions of the waveform (the portions above the dashed lines) indicate that the current is flowing in a positive direction, while the negative portions (below the dashed lines) indicate that current is flowing in a negative direction. Note that in the preferred unipolar stepper motor, the currents corresponding to phases A and A' ($\overline{A}$) actually flow in separate portions of the stator A winding, as shown in FIG. 3A, with the positive (+) current flowing through the left-hand portion of the winding and the negative (−) portion flowing through the right-hand portion of the winding.

The state next transitions to a state 156, as shown in FIG. 7. This transition occurs when $X_1'+X_2'$ is true (the "+" indicates that $X_1'$ and $X_2'$ are logically "OR"ed), i.e., the stepper motor is deselected and/or the motor phase signal $X_2$ is low. $X_2$ is switched from a logic level one to a logic level zero when the CPU determines that a motor phase (e.g., phase A) needs to be switched from a positive current to a negative current, corresponding to a predetermined timing sequence and corresponding to the M_PHA_IN input signal. For example, the M_PHA_IN signal comprises a high-to-low step change 157 at a timing mark 159 (in FIG. 9). Accordingly, since it is desired to have substantially zero current in a motor winding when the winding is switched between an energized state and a de-energized state, the current in the motor winding must be ramped down to a zero current level before the motor phase is switched. This ramp down is performed while in state 156.

Upon entering state 156, $Z_3$ is switched to high, thereby enabling an input to be received by the digital potentiometer, while $Z_4$ is set to low, thereby causing the 5-bit up/down counter in the digital potentiometer to count down when it receives the 23 kHz clock signal on its increment pin. At the same time, the 8-bit synchronous up counter is reset to 27 and counts upward until it reaches 64, whereupon $X_3$ goes high; this results in the increment pin receiving 36 pulses, in a manner similar to that discussed above when ramping the digital potentiometer upward. This causes the voltage output at the digital potentiometer's wiper to be ramped downward until the output voltage is reduced to zero volts, as shown by a downwardly-ramped portion 161 of the MI_STA current reference command signal (FIG. 9).

When $X_3$ goes high (indicating that the ramping has been completed) the present state transitions to a state 158. In state 158, the current reference command signal remains at zero volts, thereby creating zero current (ideally) in the stator A motor winding.

In the case of the timing diagram of FIG. 9, the system remains in state 158 for only a single clock cycle, whereupon it is caused to transition back to state 152 when $X_1 \cdot X_2'$ is true (i.e., the motor is selected and motor phase A is low), a condition that has existed since timing mark 159. At this point, the voltage ramp-up process described above is repeated, but this time, X2 (and thus Z2) is low, causing the winding current to flow in the reverse direction from its previous direction of flow, as indicated by a portion 163 of the MI_A current waveform in FIG. 9 and phase $\overline{A}$ in FIG. 3A. At the end of the voltage ramp-up, $X_3$ again goes high, while $X_1$ remains at logic level one.

In contrast to the foregoing transition from state 152 to state 154, this time, the value of $X_2$ is at logic level zero instead of one, indicating that the current direction commanded by the CPU has been reversed. As a result, when X3 goes high, X1·X2'·X3 is true, and the system transitions to a state 160 on the right-hand branch of the state diagram, which additionally leads to states 162 and 164. At each level of the diagram, the state on the left hand branch of the diagram is substantially analogous to the state on the right hand branch of the diagram, except that the direction of current flow in the Stator A motor winding is positive for the left-hand branch states (i.e., phase A, as indicated by "HOLD 1") and negative for the right-hand branch states (i.e., phase $\overline{A}$, as indicated by "HOLD 0").

The system transitions from state 160 to state 162 when X1'+X2 is true, which coincides with a timing mark 165 corresponding to a step-change 167 of the motor phase A signal M_PHA_IN (FIG. 9). As discussed above, since it is desirable to have zero current in a winding when it is switched on or off, the current reference command signal must be ramped back to zero volts. This step is performed while in state 162, in a manner substantially similar to that described above with reference to state 156, except in this instance, the current is flowing in a reverse direction.

At the end of the ramp down, $X_3$ again goes high, causing a transition to state 164, and then back to state 152 after one clock cycle. The foregoing state-transition sequence is repeated on a continuous basis, resulting in the state diagram being traversed in a figure-8 pattern.

A timing diagram corresponding to a second drive mode in accord with the state diagram is shown in FIG. 11. In this drive mode, the motor is single stepped using full-stepping at 8 ms/step, with a 2 ms peak period and I ms ramping. The solid vertical timing bars in the diagram are spaced apart so as to define 8 ms intervals.

In the drive mode of FIG. 11, the state table is traversed in a manner identical to that described above with reference to the drive mode shown in FIG. 9 during an upwardly-ramped portion 170 and a plateau portion 171 of the MI_STA signal waveform. At this point, the drive modes (and corresponding traversal of the state diagram) differ. Note that in contrast to the timing diagram in FIG. 9, motor select signal M_SEL_IN is not always on, but is rather switched on for 2 ms, and then switched off for 6 ms during every timing interval. As discussed above, the state diagram transitions from state 154 to state 156 when X1'+X2' is true. In this case, the present state is caused to transition to state 156 when the M_SEL_IN signal is switched from high-to-low, corresponding to a dashed timing mark 172.

After the ramp-down in state 156 is performed, $X_3$ goes high, and the present state transitions to state 158. At this point, since the M_SEL_IN signal is at a logic level zero, condition X1' is true, and a transition back to initialized state 150 occurs. While in this state, the current in the motor windings is turned off. The system remains in state 150 until M_SEL_IN is switched high again, whereupon the state diagram is traversed in the same pattern, i.e., through states 152→154→156→158→150. The motor current is again switched off until a timing mark 174 occurs, which coincides with the M_PHA_IN signal being switched from high-to-low, and the M_SEL_IN signal is switched back on, causing a transition again to state 152. However, in contrast to the first two timing intervals, M_PHA_IN is now low, so that as the MI_STA current reference command signal is ramped up, the current in the stator A winding is ramped to a maximum negative value (i.e., phase $\overline{A}$ is energized to a peak current corresponding to the plateau region of the signal). Since M_PHA_IN is low, subsequent events in the timing diagram during the third timing interval cause the state diagram to be traversed along its right-hand branch in a manner analogous to that described above. The system thus traverses states 152→160→162→164→150. This pattern is repeated during a forth timing interval, whereupon the entire sequence is re-initiated and repeated on a continuous basis.

Another difference between the drive modes of FIGS. 9 and 11 is that in the drive mode of FIG. 11, both motor phases are energized at the same time, rather than 90° out of phase. This process corresponds to a conventional single stepping drive mode, except that the currents in the windings are not rapidly switched between the full-off and full-on states.

In addition to the foregoing drive modes, the state diagram may be used to implement a drive mode (not shown) in which the plateau portion of the waveform is eliminated. As shown in FIG. 7, a transition from ramp-up state 152 to the left-hand ramp-down state 156 will occur if X1'·X2 is true, and a transition from state 152 to the right-hand ramp-down state 162 will occur if X1'·X2' is true.

The state diagram can be implemented by programming an FPGA with suitable logic. This programming is generally implemented in one of two ways, depending on the available design tools for the FPGA that is to be used. In the first method, a schematic of a logic circuit corresponding to the state diagram is designed using computer aided design tools, where the schematic includes a plurality of logic gates and conventional logic circuit elements, such as flip-flops, decoders, counters, etc. The exact circuit elements used may vary, depending on the expertise of the designer, and upon the library of circuit elements that are available for programming a particular FPGA. In one preferred design scheme, the logic circuit comprises a plurality of 8:1 multiplexers, which receive the CPU input signals after they are gated through various logic gates and D-type flip-flops. A portion of the D-type flip-flop gate logic is shown in the right-hand portion of FIG. 8. In addition, the state machine outputs $Z_1$, $Z_2$, $Z_3$, and $Z_4$ may be obtained through use of the logic equation table shown in FIG. 10. As with the foregoing equations, a "+" indicates OR logic, while a "·" indicates AND logic.

In an alternate method, the FPGA can be programmed using a hardware description language (HDL), a "C"-like language used for implementing logic in programmable gate arrays and other related logic devices. The method used in programming the FPGA will depend on the programmer's expertise and familiarity with the FPGA's design tools. In addition, although preferred, it is not required that the state diagram be implemented with an FPGA. For instance, logic for implementing the state diagram could be programmed into a microcontroller, an ASIC, or other similar programmable electronic components.

As discussed above, the current in the stepping motor windings is controlled by a peak-limited constant off-time modulator circuit, which is a type of chopper drive. Chopper drives are commonly used for driving stepper motors, especially when high-torque and/or high stepping rates are required, and include pulse-width modulated drives in addition to peak-limited constant off-time modulators. Chopper drives are high efficiency switching current regulators, which allow for adequate voltage margin to maintain current regulation, while overcoming the back emf seen at the higher motor speeds.

A schematic diagram of the peak-limited constant off-time modulator circuit is shown in FIG. 12. The modulator circuit produces a pair of modulated waveforms MOD_A and MOD_B, which are respectively used to modulate the phase A and phase B drive of the stepping motor. As shown in the Figure, the motor current command signal for phase A (MI_STA) is a signal having an amplitude of from about 0 to 2.5 volts that is set by a combination of the DAC reference voltage and the digital potentiometer wiper position. This voltage level is input on the non-inverting terminal of a comparator 202, which compares the voltage to a voltage level corresponding to a current-sense feedback signal 204, which is connected to the inverting terminal of the comparator. If the current-sense feedback voltage exceeds the command signal voltage (i.e., the sensed current exceeds the commanded current), the output of the comparator circuit will be shunted to ground (labeled "GMOT"). As a result, the voltage on the non-inverting terminal of a second comparator 206 is substantially zero. The input on the inverting terminal of comparator 206 is set to 2.5 volts, using a voltage-divider circuit comprising two 49.9 kohm precision resistors in a preferred embodiment. Since 2.5 volts is greater than zero volts, the output of comparator 206 will also be shunted to ground, thereby turning the MOD_A signal off. The output of comparator 206 will remain off for a time period of about 5 $\mu s$, which corresponds to the constant-off time interval of the circuit. This time is achieved by a resistor capacitor (RC) circuit comprising a 51 kohm resistor 208 and a 100 pF capacitor 210. This RC circuit maintains the input on the non-inverting side of comparator 206 to a value of less than 2.5 volts for the 5 $\mu s$ period such that the modulator is turned off for 5 $\mu s$ each time it detects that the phase A winding current exceeds the MI_STA commanded current. In instances where the sensed current is less than the commanded current, the shunt path to ground through comparator 206 will be removed, thereby producing a voltage on the non-inverting terminal of comparator 206 that exceeds 2.5 volts. Under this condition, the shunt path to ground in comparator 206 is removed, and the voltage on signal MOD_A is substantially equal to a 3.3 volt pull-up voltage. Thus, whenever the sensed current exceeds the commanded current, modulated signal MOD_A is turned off for 5 $\mu s$, and it is switched back to 3.3 volts until another excess current condition is sensed.

A substantially identical circuit is used for modulating the MOD_B drive signal, as shown in the lower portion of FIG. 12.

In each of the foregoing drive schemes, the DAC voltage is maintained at a constant value. It is also possible to implement one-half step and one-fourth step drive modes by programming the two DAC channels so as to produce current input signals comprising scalloped pseudo-sinusoidal waveforms. Timing diagrams for the half-step and one-fourth step drive modes are respectively shown in FIGS. 14 and 15.

FIG. 13 shows a timing diagram corresponding to a one-half step wave drive mode operating at a rate of 4 ms/step, wherein a DAC output reference voltage is maintained for 2 ms intervals. As can be seen by the DAC A waveform and the DAC B waveform, the DAC channels are programmed so as to produce a stepped waveform comprising three distinct levels corresponding to a percentage of the DAC's full-scale output voltage, including a 0% level, a 70.7% level, and a 100% level. These output levels are selected so that the resultant current command signal comprises a pseudo-sinusoid, which includes a 0° portion (sin(0°)=0), a 45° portion (i.e., one-half of the 90° electrical full-step, where sin(45°)=0.707) , and a 90° portion (where sin(90°)=1). Each portion is maintained for 2 ms or one-half step. The DAC A and DAC B waveforms can be easily produced by sending a parallel 8-bit input signal from the CPU to the DAC at up to 2 ms intervals in the preferred embodiment. Although the DAC A and DAC B current command reference signals comprise stepped waveforms, the actual current command reference signals MI_STA and MI_STB comprise a scalloped half sinusoidal waveform, due to the low-pass filter that is connected to each channel of the DAC output. The "V-shaped" waveform portions correspond to the wiper position of the digital potentiometers just prior to and after a channel's DAC voltage is reduced to 0 volts, which corresponds to points in the diagram where either the M_PHA_OUT or M_PHB_OUT signals experience a logic level change. Such changes indicate that either phase A or phase B is to be switched between an energized state and a de-energized state. In this instance, the digital potentiometer is ramped down prior to the switching operation and immediately ramped back up after the switching operation, using a 1 ms ramp period. Although not shown, the digital potentiometers' wiper positions are set to their maximum values during the remainder of the cycle. As a result of the current direction changes in the motor windings (corresponding to the M_PHA_OUT and M_PHB_OUT signal changes), the drive currents produced in the stepping motor's stator A and stator B windings comprise scalloped sinusoidal waveforms that are 90° out of phase, as respectively shown by waveforms MI_A and MI_B in FIG. 13.

FIG. 14 shows a timing diagram corresponding to a one-fourth step wave drive mode comprising five different DAC output levels. These output levels correspond to sine values at quarter-step increments, including 0%, 38%, 71%, 92%, and 100%, where the percentage corresponds to the predetermined peak amplitude. The DAC A and DAC B waveforms are 90° out of phase, and approximate sinusoidal waveforms. The "V-shaped" waveform portions correspond to downwardly and upwardly ramped digital potentiometer outputs that operate in an identical manner to that discussed above with reference to the one-half step drive mode. As a result of the low-pass filter and the increase in the number of sub-steps, the motor winding current command signals MI_STA and MI_STB comprise scalloped half sinusoidal waveforms that are somewhat smoother than the corresponding signals shown in FIG. 13. The resultant motor winding currents MI_A and MI_B approach sinusoidal waveforms, with only a small amount of scalloping. This mode results in smooth motor rotation with only a slight current ripple.

Experimental Results

FIGS. 16 and 17 show copies of printouts produced by an oscilloscope that was used to measure current levels in the motor windings during experimental testing of the trapezoidal drive mode. FIG. 15 is a vector plot comprising the currents in phases A and B during a continuous stepping (i.e., slewing) operation in which the infusion pump plunger is being retracted. Note that due to noise caused by the chopper drive, the plot appears to comprise two foreshortened circles; this plot should ideally result in a single foreshortened circle. Each 90° quadrant corresponds to a full-step of the motor. The direction of the current for a given quadrant can be determined by evaluating whether the plot-axis value is positive or negative in that quadrant. The foreshortened portions of the "circle" correspond to the plateau portions of the trapezoidal current command waveforms; theoretically, a perfect circle would result if driving an ideal stepper motor using a pair of phased sinusoidal signals for phases A vs. B. The overall smoothness of the foreshortened circle indicates that the motor torque does not include any discontinuities.

FIG. 16 is a plot of MI_PHB, MI_B, MI_STB, and DAC_B signals vs. time. This plot clearly shows that the current in the motor's phase B winding is essentially zero whenever phase B is switched on or off (the plot axis adjacent to the "2→" label corresponds to a 0 current level). These results confirm that the digital current ramping source scheme of the present invention removes the current discontinuities associated with conventional drive schemes, thereby greatly reducing resonance and noise.

Although the present invention has been described in connection with a preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A stepper motor controller for controlling a motion of a stepper motor having a plurality of windings, by selectively energizing said plurality of windings so as to control a current level in the selectively energized windings based on a predetermined motor phase sequence and a predetermined current profile, comprising:

(a) a master logic device that produces control signals corresponding to the predetermined motor phase sequence and the predetermined current profile;

(b) a slaved logic device that receives a portion of the control signals from the master logic device and in response generates ramp command signals based upon the predetermined current profile;

(c) a digital potentiometer connected to the slaved logic device to receive the ramp command signals, said digital potentiometer producing a current command signal having a voltage level ranging between a low reference voltage and a high reference voltage, as a function of the ramp command signals, said current command signal corresponding to the predetermined current profile; and (d) a stepper motor drive circuit, connected to the master logic device to receive the control signals and to the digital potentiometer to receive the current command signal, said stepper motor drive circuit controlling the current levels in the stepper motor windings in response to the control signal and the current command signal, and in accord with the predetermined motor phase sequence.

2. The stepper motor controller of claim 1, wherein the digital potentiometer comprises an up/down counter having a minimum and maximum value that stores a current count value based on the ramp command signal, whereby the current command signal varies as a function of the current count value.

3. The stepper motor controller of claim 1, further comprising a feedback circuit that monitors a current in the windings of the stepper motor.

4. The stepper motor controller of claim 3, wherein the stepper motor drive circuit comprises a chopper drive that provides a modulated current control signal to control the current level in a selectively energized winding.

5. The stepper motor controller of claim 4, wherein the chopper drive comprises a peak-limited constant off-time modulator circuit that provides the modulated current control signal based on the current command signal and the current in the windings monitored by the feedback circuit such that if the current in the windings exceeds the current command signal, the modulated current control signal is switched off for a predetermined time interval.

6. The stepper motor controller of claim 1, wherein the predetermined current profile comprises a trapezoidal waveform having a positive portion and a negative portion separated by a substantially zero current crossover point, a timing relationship between the predetermined motor phase sequence and the zero current crossover point for current through a selected winding being controlled so that the current in the selected winding is substantially zero immediately after the selected winding is switched between an energized state and a de-energized state.

7. The stepper motor controller of claim 6, wherein the trapezoidal waveform has an upwardly-ramped portion, a plateau portion, and a downwardly-ramped portion, and wherein said slaved logic device implementing a plurality of states corresponding respectively to the upwardly-ramped portion, the plateau portion, and the downwardly-ramped portion.

8. The stepper motor controller of claim 7, wherein the digital potentiometer comprises an up/down counter that stores a current count value based on the ramp command signals, said ramp command signals comprising a signal that determines whether the up/down counter counts up or down and a series of pulses that are received by the up/down counter, said current command signal varying as a function of the current count value, and wherein the upwardly-ramped and downwardly-ramped portions of the trapezoidal current command waveform are generated by the digital potentiometer by ramping the current count value.

9. The stepper motor controller of claim 8, wherein the slaved logic device tracks a current portion of the trapezoidal waveform, causing a transition to a next state upon detecting that an upwardly-ramped portion has caused the current command signal to reach the high reference voltage.

10. The stepper motor controller of claim 7, wherein the control signals produced by the master logic device comprise a motor phase command signal, and wherein a transition to a next state occurs in response to a change in the motor phase command signal.

11. The stepper motor controller of claim 1, wherein the master logic device comprises one of a microprocessor and a microcontroller.

12. The stepper motor controller of claim 1, wherein the slaved logic device comprises a programmable gate array.

13. The stepper motor controller of claim 1, further comprising a programmable voltage source that is connected to the master logic device to receive a portion of the control signals and processes said portion of the control signals to produce the high reference voltage.

14. The stepper motor controller of claim 13, wherein the programmable voltage source comprises a digital-to-analog converter.

15. The stepper motor controller of claim 13, further comprising a low-pass filter connected to an output of the programmable voltage source, said low-pass filter producing a filtered high reference voltage connected to a high reference voltage terminal of the digital potentiometer.

16. A stepper motor controller for controlling a motion of a two-phase stepper motor comprising a plurality of windings by selectively energizing said plurality of windings so as to control a current level in each of said plurality of windings based on a predetermined motor phase sequence and a predetermined current profile for the windings, comprising:
(a) a processor programmed with logic for issuing control signals that generate the predetermined current profile, said control signals including motor phase command signals corresponding to the predetermined motor phase sequence;
(b) a logic device, coupled to the processor for receiving a portion of the control signals and programmed with logic for generating ramp command signals for obtaining the predetermined current profile for each motor phase;
(c) a pair of digital potentiometers connected to the logic device to receive the ramp command signals, each digital potentiometer being associated with a different motor phase and producing an output voltage ranging between a low reference voltage and a high reference voltage as a function of the ramp command signals, such that each digital potentiometer produces current command signals corresponding to the predetermined current profile for its associated motor phase; and
(d) a stepper motor drive circuit, coupled to the processor to receive the control signals and to the pair of digital potentiometers to receive the current command signals, said stepper motor drive circuit controlling current levels in the stepper motor windings based on the current command signals and the motor phase command signals.

17. The stepper motor controller of claim 16, further comprising a two-channel digital-to-analog converter that receives a portion of the control signals from the processor and processes said portion of the control signals to produce the high reference voltage for respective channels, said high reference voltages being connected to high reference voltage terminals on the digital potentiometers.

18. The stepper motor controller of claim 17, wherein the processor implements a process for driving the stepper motor in a quarter-step mode, said quarter-step mode being enabled by programming the respective channels on the digital-to-analog converter so as to produce a pair of five-level pseudo-sinusoidal current command signals between which there is a 90° phase difference.

19. The stepper motor controller of claim 17, wherein the processor implements a process for driving the stepper motor in a half-step mode, said half-step mode being enabled by the programming respective channels on the digital-to-analog converter so as to produce a pair of three-level current command signals between which there is a 90° phase difference.

20. A method for driving a stepper motor comprising a plurality of windings corresponding to respective motor phases that are selectively energized in a predetermined motor phase sequence to rotate the stepper motor, the method comprising the steps of:
(a) generating motor phase command signals corresponding to the predetermined motor phase sequence, and ramp command signals corresponding to a predetermined trapezoidal winding current waveform that includes an upwardly sloped portion, a plateau portion, and a downwardly-sloped portion connected in a sequence;
(b) generating a trapezoidal current command signal corresponding to the predetermined trapezoidal winding current waveform by controlling a digital potentiometer with the ramp command signals; and
(c) selectively energizing windings among said plurality of windings based on the motor phase signals and the trapezoidal current command signal so as to control a current level in said selectively energized windings that corresponds to the trapezoidal current command signal.

21. The method of claim 20, wherein the stepper motor comprises a unipolar stepper motor.

22. The method of claim 20, wherein the ramp command signals are generated to control a transition between a plurality of states, including states respectively corresponding to said upwardly-sloped, plateau, and downwardly-sloped portions of the trapezoidal waveform, and wherein the transition between the plurality of states occurs in response to the motor phase command signals.

23. The method of claim 20, wherein the current levels in the selectively energized windings are controlled to follow the trapezoidal current command signal by using a chopper drive circuit that employs a current-sense feedback signal.

24. The method of claim 23, further comprising the steps of:
(a) continuously comparing the trapezoidal current command signal with the current-sense feedback signal;
(b) energizing the selectively energized windings by connecting a drive voltage to said selectively energized windings as long as the trapezoidal current command signal exceeds the current-sense feedback signal; and
(c) disconnecting said selectively energized windings from the drive voltage for a predetermined time interval whenever the current-sense feedback signal exceeds the trapezoidal current command signal.

25. The method of claim 20, wherein the predetermined trapezoidal winding current waveform comprises a positive portion and a negative portion separated by a substantially zero current crossover point, and wherein a timing relationship between the predetermined motor phase sequence and the zero current crossover point for current through a selected winding is controlled so that the current in the selected winding is substantially zero immediately after the selected winding is switched between an energized state and a de-energized state.

26. The method of claim 20, wherein the predetermined trapezoidal winding current waveform comprises rise and fall times corresponding to a stepping rate of the motor.

27. A method for driving a stepper motor comprising a plurality of windings corresponding to respective motor phases that are selectively energized in a predetermined motor phase sequence to rotate the stepper motor, the method comprising the steps of:

(a) generating motor phase command signals corresponding to the predetermined motor phase sequence;

(b) generating control signals to produce a current command signal having zero current portions, first step portions with a current level greater than the zero current portions, and a maximum current portion, wherein an upwardly-ramped portion connects a zero current portion to a first step portion, and a downwardly-ramped portion connects another first step portion to another zero current portion; and (c) selectively energizing windings among said plurality of windings based on the motor phase signals and the current command signal so as to control a current level in said selectively energized windings that corresponds to the current command signal.

28. The method of claim 27, further including the step of generating a ramp command signal, and wherein the upwardly--ramped and downwardly-ramped portions of the current command signal waveform are generated by controlling a digital potentiometer in response to the ramp command signal.

29. The method of claim 27, wherein the stepped portions of the current command signal waveform are generated by controlling a digital-to-analog converter so as to produce the stepped portions.

30. The method of claim 29, further comprising the step of filtering the output signal produced by the digital-to-analog converter with a low-pass filter, thereby producing a current command signal waveform comprising a sequence of scalloped half-sinusoidal waveforms connected by the zero current portions.

31. The method of claim 30, wherein the stepped half-pseudo-sinusoidal waveforms comprise second step portions and third step portions, each of said second step portions having a current level greater than the current level of the first step portions, and each of said third step portions having a current level greater than the second step portions.

* * * * *